(12) United States Patent
Fairley et al.

(10) Patent No.: US 10,149,885 B2
(45) Date of Patent: Dec. 11, 2018

(54) METHOD OF TREATMENT OR PROPHYLAXIS OF INFECTIONS OF THE EYE

(71) Applicant: STARPHARMA PTY LIMITED, Abbotsford, Victoria (AU)

(72) Inventors: Jacinth Kincaid Fairley, Hawthorn (AU); Colin Paul Barrett, Hampton (AU); Jeremy Robert Arthur Paull, Burwood (AU)

(73) Assignee: STARPHARMA PTY LIMITED, Abbotsford (AU)

( * ) Notice: Subject to any disclaimer, the term of this patent is extended or adjusted under 35 U.S.C. 154(b) by 0 days.

(21) Appl. No.: 14/427,970

(22) PCT Filed: Sep. 13, 2013

(86) PCT No.: PCT/US2013/059810
§ 371 (c)(1),
(2) Date: Mar. 13, 2015

(87) PCT Pub. No.: WO2014/043576
PCT Pub. Date: Mar. 20, 2014

(65) Prior Publication Data
US 2015/0238557 A1    Aug. 27, 2015

Related U.S. Application Data

(60) Provisional application No. 61/700,714, filed on Sep. 13, 2012.

(51) Int. Cl.
| | |
|---|---|
| *A61K 38/08* | (2006.01) |
| *A61K 9/00* | (2006.01) |
| *A61K 31/795* | (2006.01) |
| *A61K 47/59* | (2017.01) |

(52) U.S. Cl.
CPC ............ *A61K 38/08* (2013.01); *A61K 9/0048* (2013.01); *A61K 31/795* (2013.01); *A61K 47/59* (2017.08)

(58) Field of Classification Search
CPC .................. A61K 31/795; A61K 38/08; A61K 47/48192; A61K 9/0048
USPC ............... 514/2.3, 2.4, 2.6, 2.7, 2.8, 3.7, 4.2
See application file for complete search history.

(56) References Cited

U.S. PATENT DOCUMENTS

| | | | |
|---|---|---|---|
| 6,190,650 B1* | 2/2001 | Matthews | A61K 31/785 424/78.17 |
| 6,464,971 B1 | 10/2002 | Matthews et al. | |
| 2006/0204532 A1* | 9/2006 | John | A61M 25/0026 424/422 |
| 2009/0118467 A1* | 5/2009 | Krippner | A61K 31/785 530/323 |
| 2010/0226963 A1* | 9/2010 | Cooper | A61K 9/0043 424/429 |
| 2010/0252050 A1 | 10/2010 | Grogan et al. | |
| 2012/0295839 A1 | 11/2012 | Paull et al. | |

FOREIGN PATENT DOCUMENTS

| | | |
|---|---|---|
| CN | 1154123 A | 1/2004 |
| WO | WO 95/34595 | 12/1995 |
| WO | WO 00/03710 | 1/2000 |
| WO | WO 00/15240 | 3/2000 |
| WO | WO 02/079299 A1 | 10/2002 |
| WO | WO 2005/099715 A2 | 10/2005 |
| WO | WO 2007/045009 A1 | 4/2007 |
| WO | WO 2009/046446 A2 | 4/2009 |
| WO | WO 2011/003876 A1 | 1/2011 |

OTHER PUBLICATIONS

Gajbhiye et al. (Journal of Pharmacy and Pharmacology 2009; 61: 989-1003).*
Gajbhiye, V. et al., "Dendrimers as therapeutic agents: a systematic review", Journal of Pharmacy and Pharmacology, 2009, vol. 61, pp. 989-1003.
Dzmitruk, V., et al., "Dendrimers in anti-HIV therapy," Advances in Nanocomposite Technology, InTech, 2011, ISBN 978-953-307-347-7, pp. 361-374.
International Search Report and Written Opinion dated Dec. 26, 2013 for PCT/US2013/059810.
Lopez, Analette I. et al., "Antibacterial activity and cytotoxicity of PEGylated poly(amidoamine) dendrimers," Mol. BioSyst., 2009, 5, 1148-1156.
Rupp, Richard et al., "VivaGel™ (SPL7013 Gel): A candidate dendrimer—microbicide for the prevention of HIV and HSV infection," International Journal of Nanomedicine, 2007:2(4) 561-566.
Extended European Search Report dated Feb. 23, 2016 for EP Application No. 13837849.
International Preliminary Report on Patentability dated Mar. 17, 2015 for PCT/US2013/059810.
Roba, Laurie A., et al. "Adenoviral ocular isolates demonstrate serotype-dependent differences in in vitro infectivity titers and clinical course." *Cornea* 14.4 (1995): 388-393.
Patton, et al., "A summary of preclinical topical microbicide vaginal safety and chlamydial efficacy evaluations in a pigtailed macaque model", Sex Trans Dis. Dec. 2008 v35, No. 12, 9 pages.
McGowan, et al. "Phase 1 randomized trial of the vaginal safety and acceptability of SPL7013 gel (VivaGel) in sexually active young women (MTN-004)", AIDS, 25, (2011) 1057-1064.

(Continued)

*Primary Examiner* — Johann R Richter
*Assistant Examiner* — Courtney A Brown
(74) *Attorney, Agent, or Firm* — Knobbe, Martens, Olson & Bear, LLP

(57) ABSTRACT

A microbial infection in an eye of a subject is treated or prevented by topically administering to the eye an effective amount of a macromolecule or a pharmaceutically acceptable salt thereof that includes a dendrimer of 1 to 8 generations with one or more sulfonic acid- or sulfonate-containing moieties attached to one or more surface groups of the outermost generation of the dendrimer. Compositions containing the macromolecule or salt are useful in these methods.

43 Claims, No Drawings

(56) References Cited

OTHER PUBLICATIONS

O'Loughlin, et al., "Safety, Tolerability, and Pharmacokinetics of SPL7013 Gel (VivaGel): A Dose Ranging, Phase I Study", Sexually Transmitted Diseases, 37(2), (2010), 100-104.

Cohen et al., "A phase I randomized placebo controlled trial of the safety of 3% SPL7013 gel (VivaGel) in health young women administered twice daily for 14 days", PLoS ONE, Jan. 2011, vol. 6, No. 1, e16258, 9 pages.

Yavuz et al. "Dendrimeric Systems and Their Applications in Ocular Drug Delivery", The Scientific World Journal, vol. 2013, Article ID 732340, 13 pages.

Bernstein, et al. "Evaluations of unformulated and formulated dendrimer-based microbicide candidates in mouse and guinea pig models of genital herpes." Antimicrobial agents and chemotherapy 47.12 (2003): 3784-3788.

Bourne, et al. "Dendrimers, a new class of candidate topical microbicides with activity against herpes simplex virus infection." Antimicrobial agents and chemotherapy 44.9 (2000): 2471-2474.

Chen et al. "A randomized, controlled trial of the safety of candidate microbicide SPL7013 Gel, when applied to the penis." J Acquir Immune Defic Syndr. Apr. 1, 2009; 50(4): 375-380.

Gong, et al. "Evaluation of dendrimer SPL7013, a lead microbicide candidate against herpes simplex viruses." Antiviral research 68.3 (2005): 139-146.

Lackman-Smith, et al. "Development of a comprehensive human immunodeficiency virus type 1 screening algorithm for discovery and preclinical testing of topical microbicides." Antimicrobial agents and chemotherapy 52.5 (2008): 1768-1781.

McCarthy, et al. "Dendrimers as drugs: discovery and preclinical and clinical development of dendrimer-based microbicides for HIV and STI prevention." Molecular pharmaceutics 2.4 (2005): 312-318.

Mumper, et al. "Formulating a sulfonated antiviral dendrimer in a vaginal microbicidal gel having dual mechanisms of action." Drug development and industrial pharmacy 35.5 (2009): 515-524.

Price, et al. "SPL7013 Gel (VivaGel®) retains potent HIV-1 and HSV-2 inhibitory activity following vaginal administration in humans." PLoS One 6.9 (2011): e24095.

Telwatte, et al. "Virucidal activity of the dendrimer microbicide SPL7013 against HIV-1." Antiviral research 90.3 (2011): 195-199.

Tyssen, et al. "Structure activity relationship of dendrimer microbicides with dual action antiviral activity." PLoS one 5.8 (2010): e12309.

* cited by examiner

METHOD OF TREATMENT OR PROPHYLAXIS OF INFECTIONS OF THE EYE

CROSS REFERENCE TO RELATED APPLICATIONS

This application is the U.S. National Phase of International Application No. PCT/US2013/059810, filed Sep. 13, 2013, designating the U.S. and published in English as WO 2014/043576 on Mar. 20, 2014 which claims the benefit of U.S. Provisional Application 61/700,714, filed Sep. 13, 2012. Any and all applications for which a foreign or domestic priority claim is identified in the Application Data Sheet as filed with the present application are hereby incorporated by reference under 37 CFR 1.57.

FIELD OF THE INVENTION

The present invention relates to methods of treating or preventing microbial infections of the eye or alleviation or prophylaxis of one or more symptoms of microbial infections of the eye. Methods of preventing the spread of microbial infections of the eye and compositions for treating or preventing microbial infections of the eye are also described.

BACKGROUND OF THE INVENTION

Conjunctivitis, also known as pinkeye, is an infection of the outermost layer of the eye, the conjunctiva, the inner surface of the eyelids or both the conjunctiva and the inner surface of the eyelids. Conjunctivitis may be caused by viruses, bacteria, allergens or chemicals. Conjuctival infections can lead to the involvement and inflammation of other parts of the eye including the cornea, sclera, lacrimal glands, meibomian glands and eye lash follicles.

Conjunctivitis caused by pathogens such as viruses (typically adenovirus, herpesvirus, coxsackie virus, pox virus and Epstein Barr virus) and bacteria is transmitted through contact of the eye with infected particles, droplets, contact lenses, medical or ophthalmic equipment. Adenovirus can be transmitted by respiratory droplets from a cough or sneeze of a person who is suffering an adenovirus respiratory infection. Inadequately sterilized contact lenses, medical or ophthalmic instruments may also cause conjunctival infection.

Adenovirus infection may rapidly spread through schools and childcare centres where children come into close contact with each other. In turn, children may infect other members of the family including siblings and parents. Although any microbe can cause inflammation of the outer eye, it has been estimated that up to 92% of diagnoses are due to adenovirus-associated epidemic keratoconjunctivitis (EKC).

Herpes zoster ophthalmicus is also a common complication of chicken pox. Of about 1 million cases of chicken pox diagnosed each year, about 250,000 develop herpes zoster ophthalmicus and half of these patients further develop complications of herpes zoster ophthalmicus.

Herpetic keratoconjunctivitis can result from both primary and recurrent Herpes Simplex Virus-1 (HSV-1) infection in adults and children. HSV-1 is almost universally acquired and is the most common form of corneal blindness in developed countries. Additionally, HSV-2 can result in Herpetic keratoconjunctivitis, primarily in neonates, who contract the infection passing through the birth canal of an infected individual.

Furthermore, not just viruses such as HSV-1, but also bacteria such as *Neisseria gonorrhoeae* and *Chlamydia* spp. may infect the eyes of neonates that have been born by passing through the birth canal of an infected mother. Such infection may cause pain and significant conjunctival discharge and left untreated may cause corneal ulceration.

While some instances of viral conjunctivitis resolve within 1 to 6 weeks without treatment, EKC, which is predominantly a result of infection with adenovirus subtypes 8, 19 and/or 37, is extremely contagious and may progress to involve the cornea as well as the conjunctiva. Involvement of the cornea affects short term vision and sometimes long term vision. Visual impairment may persist for months if subepithelial corneal infiltrates (nummuli), containing viral matter, develop. These generally require treatment with corticosteroids for a period of 4 months. EKC may also result in damage to cells responsible for tear production located in the conjunctiva resulting in long term lachrymal difficulties such as dry eye syndrome. EKC quickly spreads through a population, particularly those where large numbers of people are gathered together at close proximity such as in schools, childcare centres, hospitals, elderly care units, doctors' offices, military bases, offices and factories.

In otherwise healthy patients, conjunctivitis may resolve itself over time. However, in immunocompromised or immunosuppressed patients, such as those with HIV or hereditary immunodeficiencies, cancer patients undergoing chemotherapy, solid organ transplant or stem cell transplant recipients, significant infection and life threatening complications may result.

While conjunctivitis, especially viral conjunctivitis, primarily affects one eye, transmission to the other eye is common, particularly considering that an average person involuntarily touches their eyelids and tarsal conjunctiva about 14 times per day and this is increased in those who apply eye cosmetics and/or wear contact lenses.

Conjunctivitis can lead to blurred vision, loss of vision and in some cases pain as well as ongoing dry eye syndrome if loss of tear producing cells occurs.

Conventional therapies for conjunctivitis include topical use of non-steroidal anti-inflammatory medications, antibiotic eye drops or ointments and in severe viral infection topical corticosteroids and/or oral antiviral treatment. However, many of these treatments are not effective or are only moderately effective and need frequent administration or administration within 72 hours of onset of symptoms. Conventional eyedrops also include preservatives that may cause eye irritation in those suffering from conjunctivitis and unpreserved solutions are suitable for one use only or must be refrigerated. Conventional therapies have toxicity profiles that limit their use. Furthermore, there are no effective anti-viral agents available for treating adenoviral conjunctivitis topically. Conventional therapies are also not suitable for prophylactic use and therefore do not reduce or inhibit the spread of infection to the other eye of an individual or in those populations at risk of contracting a conjunctival infection.

Conventional therapies are typically tailored to the type of infection, bacterial or viral and are not suitable for treatment of both viral and bacterial infection simultaneously. However, it is sometimes difficult in practice to distinguish whether a patient has a viral or bacterial infection. Practitioners will treat with antibiotics due to an inability to identify the etiology and the absence of effective low toxicity topical antivirals and consequently there is much unnecessary prescribing of antibiotics. Co-infection with viral and bacterial pathogens also requires multiple therapies to be administered.

The frequency of infection is increased in contact lens wearers due to increased eye contact and the presence of a foreign body. Suspension of contact lens wear is generally required while being treated with conventional therapies as the lens may act as a nidus for the infective agent, irritate the condition and prevent treatments from reaching or remaining on the relevant area of the eye.

Since eye infections such as conjunctivitis result in significant social and economic effects including loss of school days and loss of work days, alternative therapies for treatment and especially the prophylaxis of eye infections such as conjunctivitis are required.

SUMMARY OF THE INVENTION

In a first aspect of the present invention, there is provided a method of treating or preventing a microbial infection in an eye of a subject comprising topically administering to the eye an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In a particular embodiment, the microbial infection causes conjunctivitis. In some embodiments, the conjunctivitis is viral conjunctivitis, especially viral conjunctivitis caused by adenovirus, more especially viral conjunctivitis caused by adenovirus subtypes 8, 11, 19, 37, 53, 54, 56 and 64 most especially subtypes 19 and 37.

In another aspect of the invention there is provided a method of alleviating, reducing or halting the progression of one or more symptoms of a microbial infection of an eye in a subject comprising topically administering to the eye an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In a particular embodiment, the symptoms relieved are one or more of eye redness, itching, irritation, photophobia, pain, vision impairment, swelling, watery eyes and discharge.

In a further aspect, there is provided a method of treating or preventing concurrent or undifferentiated viral and/or bacterial infection in an eye of a subject, comprising topically administering to the eye an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In yet a further aspect of the invention, there is provided a method of preventing or reducing the severity of a microbial infection in a second eye of a subject having a microbial infection in their first eye, comprising topically administering to the second eye an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In yet another aspect of the invention, there is provided a method of reducing spread of a microbial infection of an eye in a population of subjects at risk of contracting the microbial infection of an eye comprising topically administering to at least one eye of at least one subject within the population an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In another aspect of the invention there is provided a method of treating or preventing infectious conjunctivitis in a subject, comprising topically administering to an eye of the subject an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer for more than 7 days.

A composition comprising a dendrimer of 1 to 8 generations with one or more sulfonic acid- or sulfonate-containing moieties attached to one or more surface groups of the outermost generation of the dendrimer as a main ingredient is useful in connection with any of the methods of the foregoing aspects and embodiments of the invention. The dendrimer can be provided as a "main ingredient" of the composition. In this context, the dendrimer functions as "a main ingredient" when it is active to at least assist in achieving the desired result of the method.

In a further aspect of the invention, there is provided a contact lens solution comprising a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In yet a further aspect of the invention, there is provided a composition comprising a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer and at least one pharmaceutically acceptable carrier that provides pH and osmolality compatible with the eye.

In a further aspect of the invention, there is provided a microbicidal delivery system comprising a contact lens and a macromolecule or a pharmaceutically acceptable salt thereof comprising a dendrimer of 1 to 8 generations with one or more sulfonic acid- or sulfonate-containing moieties attached to one or more surface amino groups of the outermost generation of the dendrimer.

DESCRIPTION OF THE INVENTION

The articles "a" and "an" are used herein to refer to one or to more than one (i.e. to at least one) of the grammatical object of the article. By way of example, "an element" means one element or more than one element.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "about" refers to a quantity, level, value, dimension, size, or amount that varies by as much as 30%, 25%, 20%, 15% or 10% to a reference quantity, level, value, dimension, size, or amount.

In a first aspect of the present invention there is provided a method of treating or preventing a microbial infection in an eye of a subject comprising topically administering to the eye an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

The microbial infection may infect any part of the outer eye including the conjunctiva, eye lids, sclera, cornea, lacrimal apparatus, meibomian glands, eye lash follicles, plica semilunaris and lacrimal caruncle and affect other parts of the eye, which may become inflamed such as the cornea, resulting in keratitis, and the eyelids, resulting in blepharitis. In particular embodiments, the microbial infection causes infective conjunctivitis. The microbial infection may be an infection of epithelial cells or stromal cells such as keratocytes, or fibroblast cells.

The conjunctivitis may be any inflammation of the conjuctiva and/or inner surface of the eyelids. The conjunctivitis may be caused by microbe such as a virus, bacteria or fungi. In particular embodiments, the pathology of the conjunctivitis is selected from viral conjunctivitis or bacterial conjunctivitis, more especially viral conjunctivitis. The conjunctivitis may be chronic or acute. In some embodiments, the conjunctivitis is selected from epidemic keratoconjunctivitis, keratoconjunctivitis, acute hemorrhagic conjunctivitis, pharyngoconjunctival fever, pinkeye, acute epidemic conjunctivitis, swimming pool conjunctivitis, trachoma, granular conjunctivitis keratitis, Egyptian ophthalmia, non-gonococcal bacterial conjunctivitis, gonococcal conjunctivitis, inclusion conjunctivitis, chlamydial conjunctivitis, rikettsial conjunctivitis, phlyctenulosis (phlycentular keratoconjunctivitis) and blepharoconjunctivitis, especially epidemic keratoconjunctivitis, acute epidemic conjunctivitis, pharyngoconjuctival fever, pinkeye, keratoconjunctivitis, swimming pool conjunctivitis, granular conjunctivitis and acute hemorrhagic conjunctivitis. In some embodiments, the conjunctival infection has spread to other parts of the outer eye such as the cornea, sclera and/or lacrimal glands.

In some embodiments, the viral conjunctivitis is caused by one of the following viral pathogens: adenovirus including adenovirus subtypes 1, 2, 3, 4, 5, 6, 7, 8, 9, 10, 11, 13, 14, 15, 16, 17, 19, 20, 21, 22, 23, 24, 25, 26, 27, 28, 29, 30, 32, 33, 36, 37, 38, 39, 42, 43, 44, 45, 46, 47, 48, 49, 50, 51, 53, 54, 56 and 64, especially adenovirus subtypes 1, 2, 3, 4, 6, 7, 8, 11, 14, 19, 21, 37, 53, 54, 56 and 64, more especially adenovirus subtypes 3, 4, 7, 8, 11, 19, 37, 53, 54, 56 and 64, especially 8, 19, 37 and 64, most especially 19 and 37, adenovirus species D, enterovirus such as enterovirus 8, enterovirus 19 and enterovirus 70, herpes virus such as herpes simplex virus type one, herpes simplex virus type two, herpes simplex virus type three (herpes varicella-zoster virus) and herpes simplex virus type five (cytomegalovirus), coxsackie virus such as coxsackie A24 and coxsackie virus A28, rhinovirus and influenza virus including influenza Type A, such as H1N1, H7N7, H2N2, H3N2 and H5N1, influenza Type B and influenza Type C, avian influenza and swine influenza, especially adenovirus, herpes virus and coxsackie virus, more especially adenovirus or herpes virus, most especially adenovirus.

In particular embodiments, the method of the invention provides a method of treating or preventing conjunctivitis or infection and resultant inflammation of conjunctiva together with other ocular tissues such as sclera, eyelids, cornea, caused by adenovirus. In another particular embodiment, the method of the invention provides a treatment of conjunctivitis caused by a herpes virus.

In some embodiments, the bacterial conjunctivitis is caused by one or more of the following bacterial pathogens: *Neisseria* spp. such as *Neisseria gonorrhoeae* and *Neisseria meningitidis*, *Streptococcus* spp. such as *Streptococcus pneumoniae* and *Streptococcus pyrogenes*, *Staphylococcus* spp. such as *Staphylococcus aureus* and *Staphylcoccus epidermidis*, *Haemophilus* spp. such as *Haemophilus aegyptus* and *Haemophilus influenzae*, *Pseudomonas* spp. such as *Psecudomonas aeruginosa*, *Rickettsia* spp. such as *Rickettsia prowazekii*, *Moraxella lacunata*, *Listeria monocvtogenes*, *Acinetobacter iwoffi*, *Escherichia coli*, *Bacillus cereus*, *Corynebacterium* such as *Corynebacterium diphtheriae*, *Mycobacterium* spp. such as *Mycobacterium tuberculosis* and *Mycobacterium foruitum*, and *Chlamydia* spp. such as *Chlamydia oculogenitalis*, *Chlamydia trachomatis*, *Chlamydia lymphogranulomatis* and *Chlamydia psittaci*, especially *Neisseria* spp. *Chlamydia* spp., *Staphylococcus* spp., *Streptococcus* spp., *Pseudomonas* spp. and *Haemophihts* spp.

In some embodiments, the fungal conjunctivitis is caused by one or more of the following fungal pathogens: *Aspergillus* spp. such as *Aspergillus niger*, *Candida* spp. such as *Candida albicans*, *Rhinosporidium seeberi*, *Coccidioides* spp. such as *Coccidioides immitis* and *Sporothrix* spp. such as *Sporothrix schenckii*, especially *Aspergillus niger* and *Candida Albicans*.

As used herein, the term "subject" refers to any subject susceptible to conjunctivitis including humans, domesticated animals such as cats and dogs, farm animals including cattle, sheep, goats, pigs, chickens, geese, llamas, deer, and the like, laboratory test animals such as mice, rats, monkeys, rabbits and guinea pigs, wild confined animals such as those found in zoos. In a particular embodiment, the subject is a human, including neonate, child and adult.

In some embodiments, the subject is non-immunocompromised. In other embodiments, the subject is immunocompromised or immunosuppressed. Immunocompromised subjects include those that are immunodeficient such as those with HIV or hereditary immunodeficiencies and those having therapy that compromises immunity such as cancer patients being treated with chemotherapy or radiotherapy. Immunosuppressed subjects include those taking immunosuppressive drugs, for example solid organ transplant recipients or stem cell transplant recipients.

In some embodiments, the subject is a contact lens wearer. The contact lens worn may be a gas permeable (GP) lens or soft hydrogel lens of Category 1 to Category 4 (Category 1=low water, non-ionic; Category 2=high water non-ionic; Category 3=low water, ionic; Category 4=high water, ionic). Many contact lens brands exist; some of the major brands are Acuvue® Oasys® (Vistakon), Air Optix® Aqua (CIBA Vision), Biofinity® (Cooper Vision) and PureVision® (Bausch & Lomb).

The term "treatment" as used herein refers to at least partially attaining the desired therapeutic outcome but does not necessarily imply that the subject is treated until total recovery. Treatment also includes reducing or alleviating symptoms of eye infections such as infectious conjunctivitis and inflammation of related ocular tissues, especially the cornea or reducing the severity of eye infections such as infectious conjunctivitis. Treatment also includes reducing viral load or viral antigen and the period or severity of infection.

The term "prevention" refers to reducing the risk of contracting or developing eye infections such as infectious conjunctivitis or delaying the onset of eye infections such as infectious conjunctivitis. Prevention need not be complete and does not imply that a subject will not eventually contract or develop an eye infection such as infectious conjunctivitis.

An "effective amount" means an amount necessary to at least partially attain the desired response, or to delay the onset of, inhibit the progression of or halt altogether an eye infection such as infectious conjunctivitis. The amount varies depending upon the health and physical condition of the subject being treated, the taxonomic group of the subject being treated, the degree of protection required, the formulation of the composition, the infective dose, the severity of the disease and other relevant factors. It is expected that the effective amount will fall within a relatively broad range that can be determined by routine trials. An effective amount for a human patient may, for example, fall within the range of about 25 µg to 25 mg per dosage, especially 150 µg to 6 mg, more especially 0.5 mg to 2.5 mg per dosage. When in solution or as part of a composition, the macromolecule may be present in an amount of 0.1% w/w of the composition to 10% w/w of the composition, especially 0.5% to 8% w/w, more especially 1% w/w to 5% w/w of the composition.

In another aspect of the invention, there is provided a method of alleviating, reducing or halting the progression of one or more symptoms of a microbial infection of an eye and associated inflammation in a subject comprising topically administering to the eye an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In particular embodiments, the symptoms are the symptoms of conjunctivitis. As used herein, the symptoms of conjunctivitis include eye redness, itchy eyes, inflammation of eyes and eyelids, swollen eyelids, eye irritation or itching, watery eyes, or tearing (epiphora) pre-auricular lymphadenopathy, discharge, photophobia, blurred vision, plica and caruncle swelling, nummuli, dryness of the eye and astigmatism. In particular embodiments, the method of the invention alleviates or reduces eye redness, itchiness, irritation, photophobia, vision impairment, swelling, pain, watery eyes and discharge.

In some embodiments, the method of the invention reduces the severity or duration of one or more symptoms. In other embodiments, the method of the invention halts the progression of symptoms, thereby preventing further symptoms occurring or preventing a symptom getting worse.

In a further aspect, there is provided a method of treating or preventing concurrent or undifferentiated viral and/or bacterial infection of an eye in a subject, comprising topically administering to the eye an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In particular embodiments, the concurrent or undifferentiated viral and/or bacterial infection causes conjunctivitis. The term "concurrent" refers to infection by more than one microbe simultaneously. The term "undifferentiated" describes where the physician has difficulty making a specific diagnosis of the cause or etiology of the infection.

In some embodiments, the concurrent infection includes a primary viral infection and a secondary bacterial infection. In some embodiments, the concurrent infection includes a viral conjunctivitis caused by a viral pathogen selected from including adenovirus subtypes 1, 2, 3, 4, 5, 6, 7, 8, 9, 10, 11, 13, 14, 15, 16, 17, 19, 20, 21, 22, 23, 24, 25, 26, 27, 28, 29, 30, 32, 33, 36, 37, 38, 39, 42, 43, 44, 45, 46, 47, 48, 49, 50, 51, 53, 54, 56 and 64, especially adenovirus subtypes 1, 2, 3, 4, 6, 7, 8, 11, 14, 19, 21, 37, 53, 54, 56 and 64, more especially adenovirus subtypes 3, 4, 7, 8, 11, 19, 37, 53, 54, 56 and 64 especially 8, 19, 37 and 64 most especially 19 and 37, enterovirus such as enterovirus 8, enterovirus 19 and enterovirus 70, herpes virus such as herpes simplex virus type one, herpes simplex virus type two, herpes simplex virus type three, (herpes varicella-zoster virus) and herpes simplex virus type five (cytomegalovirus), coxsackie virus such as coxsackie A24 and coxsackie virus A28, rhinovirus and influenza virus including influenza Type A, such as H1N1, H7N7. H2N2, H3N2 and H5N1, influenza Type B and influenza Type C, avian influenza and swine influenza, and a bacterial conjunctivitis caused by a bacterial pathogen selected from *Neisseria* spp. such as *Neisseria gonorrhoeae* and *Neisseria meningitidis, Streptococcus* spp. such as *Streptococcus pneumoniae* and *Streptococcus pyrogenes, Staphylococcus* spp. such as *Staphylococcus aureus* and *Staphylococcus epidermidis, Haemophilus* spp. such as *Haemophilus aegyptus* and *Haemophilus influenzae, Pseudomonas* spp. such as *Psecudomonas aeruginosa, Rickettsia* spp. such as *Rickettsia prowazekii, Moraxella lacunata, Listeria monocytogenes, Acinetobacter iwoffi, Escherichia coli, Bacillus cereus, Corynebacterium* such as *Corynebacterium diphtheriae, Mycobacterium* spp. such as *Mycobacterium tuberculosis* and *Mycobacterium foruitum,* and *Chlamydia* spp. such as *Chlamydia oculogenitalis, Chlamydia trachomatis, Chlamydia lymphogranulomatis* and *Chlamydia psittaci*. In particular embodiments, the viral pathogen is selected from adenovirus, especially adenovirus subtypes 8, 19 or 37, or herpes virus and the bacterial pathogen is selected from *Neisseria* spp., *Chlamydia* spp., *Staphylococcus* spp., *Streptococcus* spp., *Pseudomonas* spp. and *Haemophilus* spp.

In some embodiments the treatment of the primary viral infection prevents a secondary bacterial infection occurring.

Advantageously, the macromolecules of the invention have both antiviral and antibacterial activity and therefore one therapy can be used to treat or prevent both infections instead of multiple therapies being required, or the physician needing to identify the cause of the infection.

Long term or incorrect use of conventional antibiotics can result in development of bacterial resistance and decreased effectiveness at clearing infection. The macromolecules of the invention advantageously have a reduced likelihood of inducing bacterial resistance.

Therefore in another aspect of the invention there is provided a method of treating or preventing conjunctivitis in a subject, comprising topically administering to an eye of the subject an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer for more than 7 days.

In some embodiments the prevention of conjunctivitis is for at least 14 days, for example, 14 to 30 days. In some embodiments the administration of the macromolecule reduces the development of bacterial resistance. In other embodiments the prevention of infectious conjunctivitis is long term to avoid recurrence of infection in individuals prone to high incidence of conjunctivitis.

In a further aspect of the invention, a subject with conjunctivitis or carrying adenoviral infection known to cause conjunctivitis is treated to prevent spread of infection to other individuals.

When a subject displays conjunctivitis, it is often in one eye. However, the infection in one eye significantly increases the risk of the infection spreading to the other eye. In most cases, in the absence of fastidious hygiene, the other eye is also infected, although often to a lesser extent. There is currently no therapy that reduces the risk of infection in the second eye.

Therefore, in yet a further aspect of the invention, there is provided a method of preventing or reducing the severity of microbial infection in a second eye of a subject having a microbial infection in their first eye, comprising topically administering to the second eye an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

Without wishing to be bound by theory, the macromolecules of the invention appear to prevent viruses infecting or entering cells, thereby reducing the likelihood of infection of the second eye with the virus.

In yet another aspect, there is provided a method of reducing the spread of microbial infection of an eye in a population of subjects at risk of contracting microbial infection of an eye comprising topically administering to at least one eye of at least one subject within the population an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In particular embodiments, the microbial infection of the eye results in conjunctivitis. Infectious conjunctivitis, especially viral conjunctivitis, is easily spread by contact, including hand-eye contact, contact with airborne droplets from coughs or sneezes, medical or ophthalmic instruments, or by contact lenses. Infectious conjunctivitis is a significant problem in populations or groups that are in close proximity, for example, schools, childcare centres, military bases, hospitals, doctors' surgeries, ophthalmic clinics, factories, offices, and the like. The rapid spread of infectious conjunctivitis in schools and childcare centres is well known where children are in close contact and there is low control over respiratory hygiene and cough etiquette.

In some embodiments, the population of subjects is a population of children, especially school children or children cared for in child care centres. In some embodiments, the population is a family or household population, including adults and children. In some embodiments, the population is a population of adults, for example, in an office or factory. In some embodiments the population is a population of adults on a military base. In some embodiments, the population is a hospital population, especially an immunocompromised population.

In some embodiments, one person in the population is administered the macromolecule of the invention. In other embodiments, all members of the population are administered the macromolecule of the invention, whether symptoms of conjunctivitis are present or not. In yet other embodiments, a proportion of the population, for example, 1 to 99% of the population are administered the macromolecule of the invention, especially at least 90%, 80%, 70%, 60%, 50%, 40%, 30%, 20% or 10% of the population are administered the macromolecule of the invention.

The macromolecule or formulation of macromolecule may be administered on a dosage regimen that provides the desired effect. For example, the formulation may be administered to the eye 1 to 6 times per day, especially 1 to 4 times per day, or 1 to 3 times per day, more especially once per day, over a period in which symptoms are present or while there is a risk of contracting an eye infection such as results in conjunctivitis. For example, dosing may occur over a period of 1 to 30 days, 1 to 20 days, 1 to 10 days, especially about 4 to 7 days.

Preventative dosing may occur once per day over 1 to 30 days, 1 to 20 days, 1 to 10 days, especially about 4 to 7 days or while the risk of contracting the microbial infection is present. Preventative dosing may occur 1 to 8 times per day. Therapeutic dosing may occur 1 to 6 times per day especially 1 to 4 times per day or 1 to 3 times per day, more especially one time per day over 1 to 30 days, 1 to 20 days, 1 to 10 days especially about 4 to 7 days or while symptoms of the microbial infection such as conjunctivitis persist.

The formulation may be co-administered in the methods of the invention with another therapy for microbial infection such as an antiviral agent, an antibiotic, an anti-inflammatory agent or a corticosteroid. Co-administration in a single composition may occur where the other therapy is compatible with the macromolecule and is suitable for topical application to the eye. Alternatively the other therapy may be delivered separately either simultaneously or sequentially. When delivered separately, the other therapy for microbial infection such as infectious conjunctivitis may be administered by any suitable means, including orally, topically or by injection.

Suitable anti-viral agents for oral administration include but are not limited to cidofovir, acyclovir, valacyclovir, famciclovir, ganciclovir, zalcitabine, alovudine, stampidine, ribavirin, cyclosporine, 2',3'-dideoxycytidine (ddC), 6-azacytidine, (S)-HPMPC, (S)-HPMPA and 2-nor-cyclic GMP.

Suitable antibiotics include amikacin, azithromycin, ceflixime, cefoperazone, cefotaxime, ceftazadime, ceftizoxime, ceftrioxone, chloramphenicol, ciprofloxacin, clindamycin, colistin, domeclocycline, erythromycin, gentamicin, mafenide, methacycline, neomycin, norfloxacin, ofloxacin, oxytetracycline, polymyxin B, pyrimethamine, rifaximin, silver sulfadiazine, sulfacetamide, sulfasoxazole, tetracycline and tobramycin.

Suitable non-steroidal anti-inflammatory drugs include salicylates such as aspirin, diflunisil and salsalate; propionic acid derivatives such as ibuprofen, dexibuprofen, fenoprofen, ketaprofen, dexketoprofen, flubiprofen, oxaprozin and laxoprofen; acetic acid derivatives such as indomethacin, tolmetin, sulindac, etodolac, keorolac, diclofenac and nabumetone; enolic acid derivatives such as piroxicam, maloxicam, tenoxicam, droxicam, lomoxicam and isoxicam; fenamic acid derivatives such as mefanamic acid, meclofenamic acid, flufenamic acid and tolfenamic acid; COX-2 inhibitors such as celecoxib, rofecoxib, valdecoxib, parecoxib, lumiracoxib, etoricoxib and firocoxib; and others such as licofelone and lysine clonixinate.

Suitable corticosteroids include hydrocortisone, hydrocortisone acetate, cortisone acetate, prednisilone, methyl prednisilone, prednisone, triamcinolore acetonide, trimcinolone alcohol, mometasome, amcinonide, budesonide, desonide, fluocinide, fluocinolone acetate, halcinonide, betamethasone, dexamethasone, fluocortolone, prednicarbate, cloberasome-17-butyrate and clobetasol-17-propionate.

Conjunctivitis may be contracted by neonates as they pass through the mother's birth canal when the mother has a viral or bacterial vaginal, cervical or labial infection. Neonates may develop the symptoms of viral conjunctivitis caused by herpes simplex virus or bacterial infection caused by gonorrhea or *chlamydia* within 1 to 5 days after birth. Prevention of transmission from mother to neonate during birth requires treatment of the mother with antibiotics or antivirals at a time sufficient before birth to cure the infection or outbreak. This is not always possible if the mother is not known to be infected or the infection is discovered immediately before or during labour.

In another aspect of the invention, there is provided a method of preventing or reducing the likelihood of transmission of bacterial or viral infection to the eyes of a neonate during passage through the birth canal of its mother, comprising administering to the birth canal of the mother, a topical formulation comprising an effective amount of a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In some embodiments, the macromolecule is administered in the form of a vaginal gel, ointment, foam, cream or lotion, especially a gel. In some embodiments, the gel formulation of macromolecule comprises a rheology modifying agent, especially a Carbopol® polymer such as Carbopol® 971P. The rheology modifier may be present in an amount of 2-10%, especially about 5%. The gel formulation of macromolecule may also include a chelating agent, such as a polyaminocarboxylic acid. A particularly useful chelating agent is ethylenediamine tetraacetic acid (EDTA) and its salts. Other ingredients that may be included in the gel formulation include preservatives such as parabens, for example methylparaben and propylparaben or mixtures thereof, solvents such as water, pH adjusting agents such as hydroxide and emollients and humectants such as glycerine and propylene glycol. A suitable formulation for vaginal application is VivaGel®.

In some embodiments, the dosage may be administered in a volume of 100 to 500 mg, especially 200 to 400 mg and more especially about 250 mg.

The dendrimers useful in the invention may be any suitable dendrimer that is capable of presenting one or more sulfonic acid- or sulfonate-containing moieties on its surface. In some embodiments, the dendrimer is selected from a polylysine, polyglutamate, polyaspartate, polyamidoamine (PAMAM), poly(etherhydroxylamine), polyether, polyester or poly(propyleneimide) (PPI) dendrimers having 1 to 8 generations. The macromolecule also comprises one or more sulfonic acid- or sulfonate-containing moiety attached to the one or more surface functional groups of the outermost generation of the dendrimer. For example, when the dendrimer is a polylysine, polyamidoamine, poly(etherhydroxylamine) or poly(propyleneimide) dendrimer, the surface functional groups are amino groups, and when the dendrimer is a polyglutamate or polyaspartate dendrimer, the surface functional groups are carboxylic acids.

Dendrimers are branched polymeric macromolecules composed of multiple branched monomers radiating from a central core moiety. The number of branch points increases upon moving from the dendrimer core to its surface and is defined by successive layers or "generations" of monomers (or building) units. Each generation of building units is numbered to indicate the distance from the core. For example, Generation 1 (G1) is the layer of building units attached to the core, Generation 2 (G2) is the layer of building units attached to Generation 1, Generation 3 (G3) is the layer of building units attached to Generation 2, Generation 4 (G4) is the layer of building units attached to Generation 3, Generation 5 (G5) is the layer of building units attached to Generation 4, and so on.

The outermost generation of building units provides the surface of the dendrimer and presents functional groups, to which the at least one sulfonic acid- or sulfonate-containing moiety is covalently bonded. The sulfonic acid- or sulfonate-containing group may be directly bonded to the surface functional group or may be attached to the surface functional group through a linker.

The dendrimers comprise one or more types of monomer unit (also referred to herein as a building unit). In particular embodiments, the dendrimers comprise one type of monomer unit. Each "branch" extending from the core of the dendrimer molecule has at least one layer or generation of building units. As used herein, the term "branch" refers to at least one generation of building units for attachment to one functional group on the core. In certain embodiments, each or any branch may have at least two layers or generations of building units. In further embodiments, each or any branch may have at least three or four layers or generations of building units. In yet further embodiments, each or any branch may independently have five layers or six or up to eight generations of building units.

The dendrimers contemplated herein can be prepared by methods known in the art and may be prepared in either a convergent manner (where, effectively, the branches are pre-formed and then attached to the core) or a divergent manner (where the layers or generations are successively built outwards from the core). Both these methods would be well understood to the skilled person.

The dendrimers may comprise any suitable core. As used herein, "core" refers to the moiety upon which generations of monomers or building units are built (either through a divergent process or a convergent process), and may be any moiety having at least one reactive or functional site from which layers of monomer or building units are successively generated (or to which a pre-formed "branch" is attached). Some exemplary suitable cores contemplated herein include those having 1, 2, 3 or 4 reactive groups independently selected from, amino, carboxyl, thiol, alkyl, alkynyl, nitrile, halo, azido, hydroxylamine, carbonyl, maleimide, acrylate or hydroxy groups to which the layers or generations of building units or monomers can be attached. A core moiety may be the same as a building unit or may be different.

Exemplary cores include polyaminohydrocarbons, disulfide containing polyamines, poly(glycidyl ethers), aminoethanol, ammonia, arylmethylhalides, piperazine, aminoethylpiperazine, poly(ethyleneimine), alkylene/arylene dithiols, 4,4-dithiobutyric acid, mercaptoakylamines, thioether alkylamines, isocyanurate, heterocycles, macrocycles, polyglycidylmethacrylate, phosphine, porphines, oxiranes, thioranes, oxetanes, aziridines, azetidines, multiazidofunctionalities, siloxanes, oxazolines, carbamates or caprolactones.

Some non-limiting examples of core moieties contemplated herein include ammonia and diamino $C_2$-$C_{12}$ alkanes such as ethylene diamine, 1,4-diaminobutane and 1,6-diaminohexane. However, it will be appreciated that the core is not necessarily a linear moiety with a single reactive group at each end. Non-linear, cyclic or branched core moieties are also contemplated by the present invention. For example, arylmethylamines such as benzhydrylamine (BHA), are suitable cores.

In some embodiments, the building units of the dendrimer are selected from lysine building units:

Amidoamine building units:

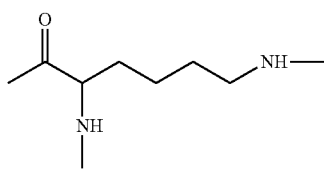

Etherhydroxyamine building units:

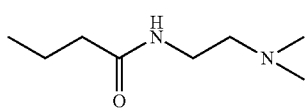

Propyleneimine building units:

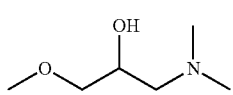

Glutamic acid building units:

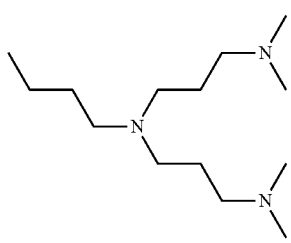 [SMILES: CCCCN(CCCN(C)C)CCCN(C)C]

Aspartic acid building units:

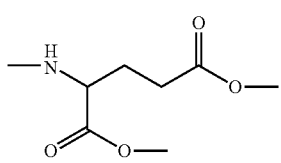

Polyester building units:

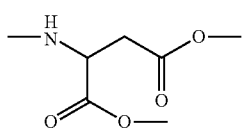

Polyether building units:

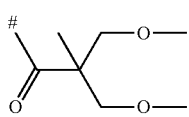

In some embodiments, the building unit may be lysine or a lysine analogue of the formula: In some embodiments, the lysine or lysine analogue is selected from a compound of the following formula:

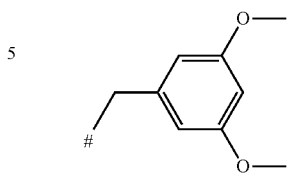

wherein K is absent or is selected from —$C_{1-6}$ alkylene-, —$C_{1-6}$ alkyleneNHC(O)—, —$C_{1-6}$ alkyleneC(O)—, —$C_{1-3}$ alkylene-O—$C_{1-3}$ alkylene-, —$C_{1-3}$ alkylene-O—$C_{1-3}$ alkyleneNHC(O)— and —$C_{1-3}$ alkylene-O—$C_{1-3}$ alkyleneC(O)—;

J is selected from CH or N:

L and M are independently absent or is selected from —$C_{1-6}$ alkylene- or —$C_{1-3}$ alkyleneOC$_{1-3}$ alkylene; provided that when L and/or M are absent, J is CH;

** indicates the linkage between the lysine or lysine analogue and the core of the dendrimer or the previous generation of building units; and

*** indicates the linkage between the lysine or lysine analogue and the subsequent generation of lysine or lysine analogues or forms the surface amino groups of the dendrimer.

Exemplary lysine analogue building units including the following:

Glycyl-Lysine 1 having the structure:

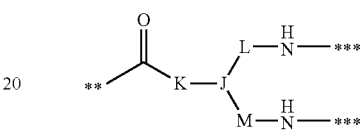

Analogue 2, having the structure below, where a is an integer 1 or 2; and b and c are independently integers 1, 2, 3 or 4:

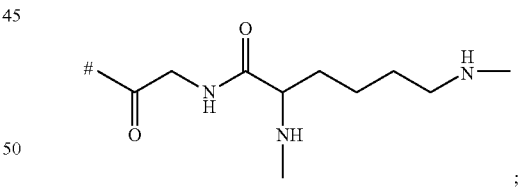

Analogue 3, having the structure below, where a is an integer 0, 1 or 2; and b and c are independently integers 2, 3, 4, 5 or 6:

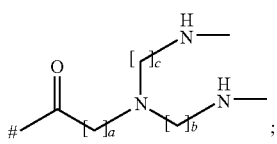

Analogue 4, having the structure below, where a is an integer 0, 1, 2, 3, 4 or 5; and b and c are independently integers 1, 2, 3, 4 or 5:

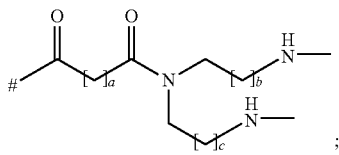

Other suitable building units include:

Analogue 5, having the structure below, where a is an integer of 0 to 2; b and c are the same or different and are integers of 1 to 4; $A_1$ and $A_2$ are the same or different and selected from $NH_2$, $CO_2H$, OH, SH, X, Allyl-X, epoxide, aziridine, $N_3$ or alkyne, where X is F, Cl, Br or I,

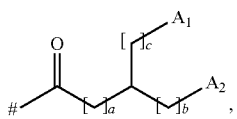

Analogue 6, having the structure below, where a is an integer of 0 to 2; b and c are the same or different and are integers of 2 to 6; $A_1$ and $A_2$ are the same or different and selected from $NH_2$, $CO_2H$, OH, SH, X, Allyl-X, epoxide, aziridine, $N_3$ or alkyne, where X is F, Cl, Br or I,

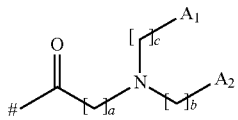

Analogue 7, having the structure below, where a is an integer of 0 to 5; b and c are the same or different and are integers of 1 to 5; $A_1$ and $A_2$ are the same or different and selected from $NH_2$, $CO_2H$, OH, SH, X, Allyl-X, epoxide, aziridine, $N_3$ or alkyne, where X is F, Cl, Br or I,

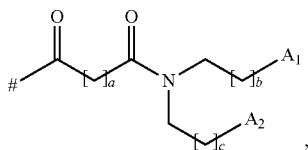

wherein each # denotes the carbonyl residue of the carboxyl group which forms an amide bond with a nitrogen atom of the core or a nitrogen atom of a previous generation of building units;

and wherein any methylene group of the building units may be replaced by a methyleneoxy ($CH_2$—O) or ethyleneoxy ($CH_2$—$CH_2$—O) group, provided that this does not result in the formation of a carbonate (—O—C(O)—O—) or carbamate (—O—C(O)—N—) moiety within the building unit.

In a particular embodiment, the dendrimer is a polylysine dendrimer having lysine building units, especially a polylysine dendrimer with a benzhydrylamine core.

The sulfonic acid-containing or sulfonate-containing moiety is any moiety that is able to present the sulfonic acid or sulfonate group on the surface of the dendrimer. In some embodiments, the sulfonic acid- or sulfonate-containing moiety has one sulfonic acid or sulfonate group. In other embodiments, the sulfonic acid- or sulfonate-containing moiety has more than one sulfonic acid or sulfonate group, for example 2 or 3 sulfonic acid or sulfonate groups, especially 2 sulfonic acid or sulfonate groups. In some embodiments, the sulfonic acid- or sulfonate-containing moiety comprises an aryl group, such as a phenyl group or naphthyl group, especially a naphthyl group.

When the sulfonate-containing moiety is present, the moiety may be present in ionic form (—$SO_3^-$) or in the form of a salt, for example, the sodium salt (—$SO_3Na$). Suitable pharmaceutically acceptable base addition salts include, but are not limited to, metallic salts such as the aluminium, calcium, lithium, magnesium, potassium, sodium and zinc salts, as well as organic salts made from organic amines such as N,N'-dibenzyl-ethylenediamine, chloroprocaine, diethanolamine, ethylenediamine, dicyclohexylamine, meglumine (N-methylglucamine) and procaine, quaternary amines such as choline, and sulphonium and phosphonium salts. In particular embodiments, salts are selected from sodium and potassium, especially sodium.

Examples of suitable sulfonic acid or sulfonate-containing moieties include but are not limited to:

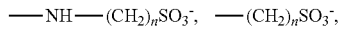

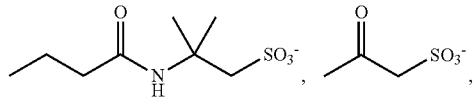

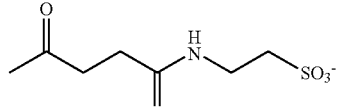

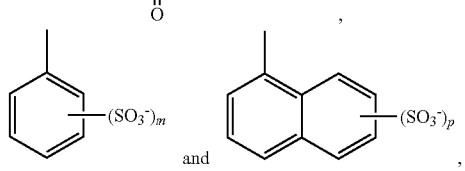

in which n is 0 or an integer of 1 to 20, m is an integer of 1 or 2 and p is an integer of 1 to 3.

In some embodiments the sulfonic acid- or sulfonate-containing moiety contains an aryl group. In some embodiments, the sulfonic acid- or sulfonate-containing moiety is selected from:

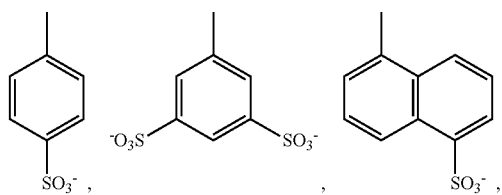

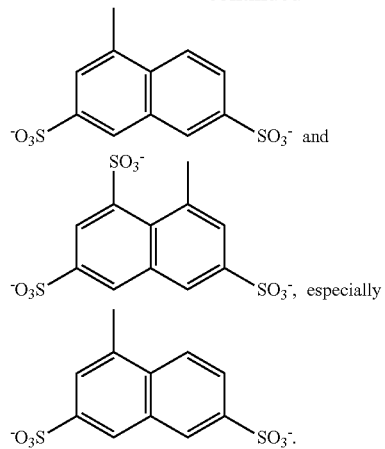

In some embodiments, the sulfonic acid- or sulfonate-containing moiety is directly bonded to the surface amino group of the dendrimer. In other embodiments, the sulfonic acid- or sulfonate-containing moiety is attached to the surface amino group of the dendrimer through a linker group.

Suitable linker groups include alkylene or alkenylene groups in which one or more non-adjacent carbon atoms is optionally replaced by an oxygen or sulfur atom to provide an ether, thioether, polyether or polythioether; or a group $-X_1-(CH_2)_q-X_2$ or $-X-(CR_1R_2)_q-X-$ wherein $X_1$ and $X_2$ are independently selected from $-NH-$, $-C(O)-$, $-O-$, $-S-$ and $-C(S)$, $R_1$ and $R_2$ are independently selected from hydrogen or $-CH_3$, and q is 0 or an integer from 1 to 10, and in which one or more non-adjacent $(CH_2)$ groups may be replaced with $-O-$ or $-S-$ to form an ether, thioether, polyether or polythioether.

In a particular embodiment, the linker is
—O—CH$_2$—C(O)—* in which # designates attachment to the sulfonic acid-containing moiety and * designates attachment to the surface amino group of the dendrimer.

Exemplary dendrimers useful in the invention include formulae I, II and III:

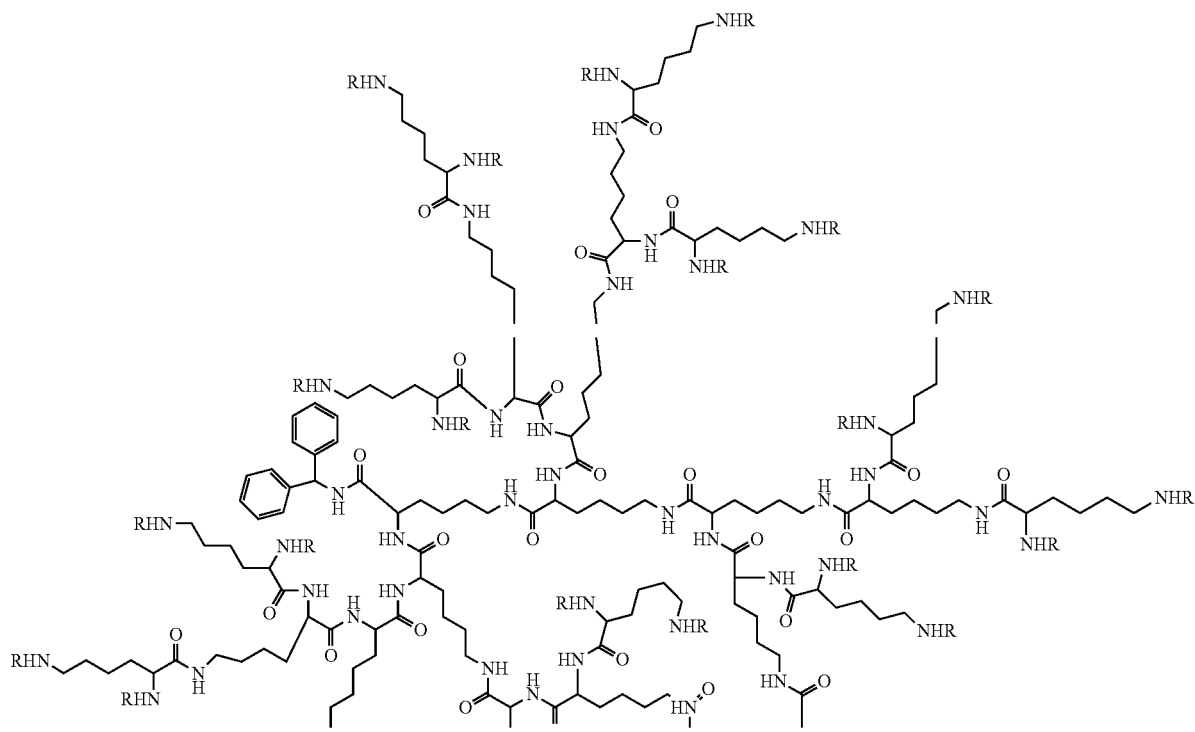

-continued
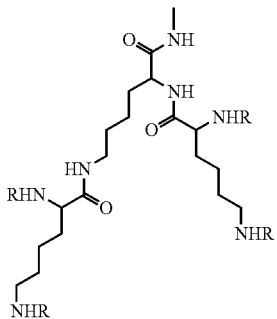
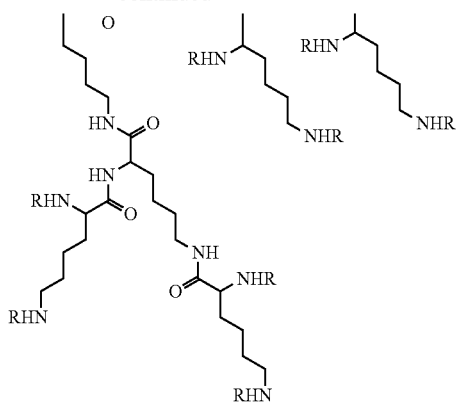
II
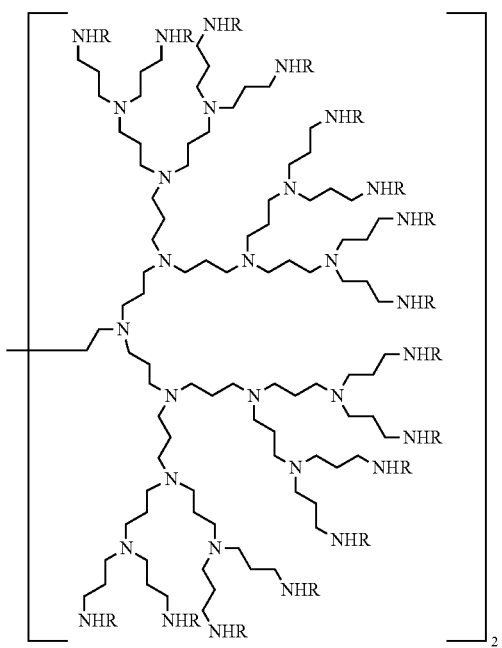

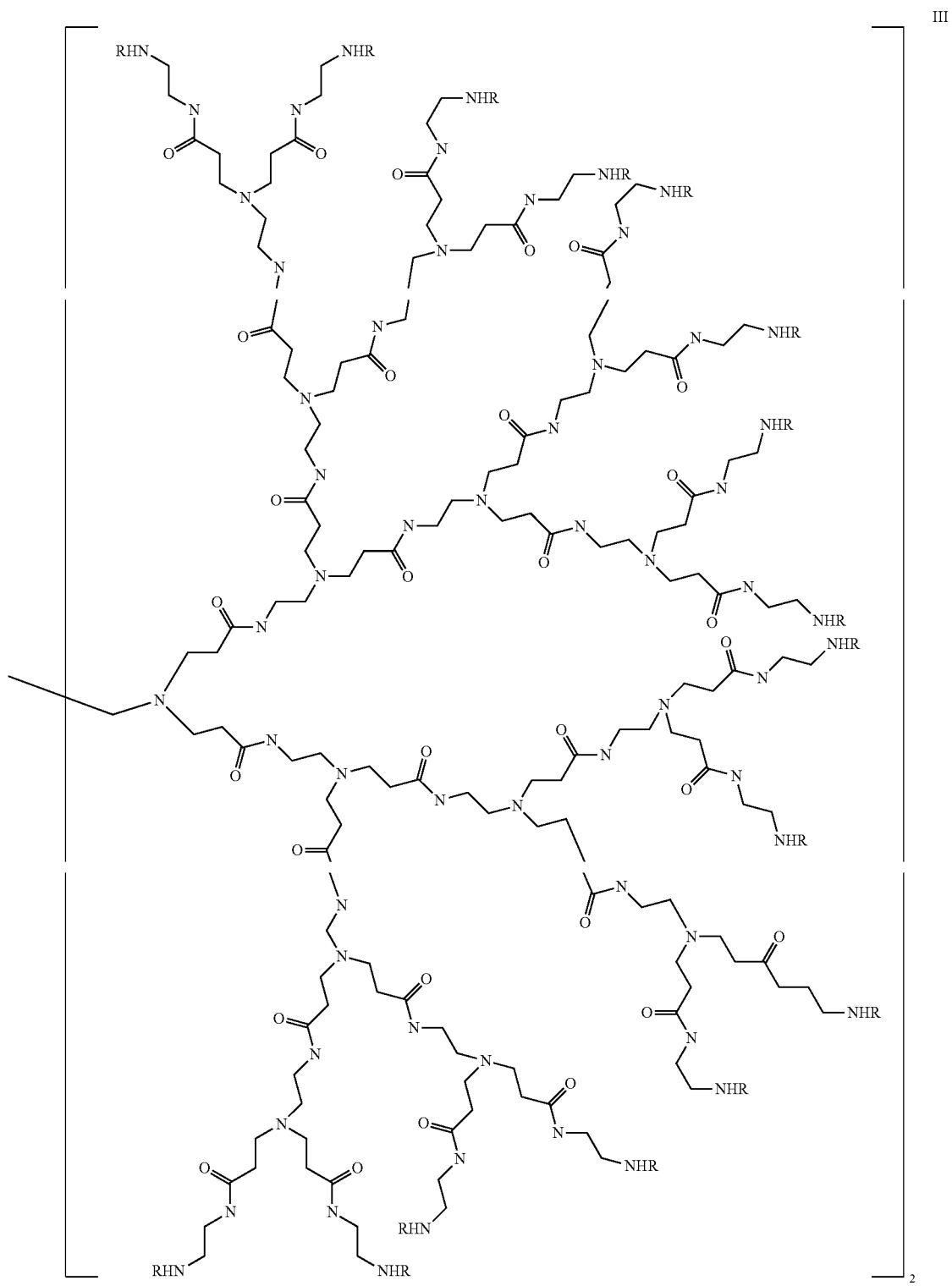

in which each R group is represented by a group formula IV or hydrogen:

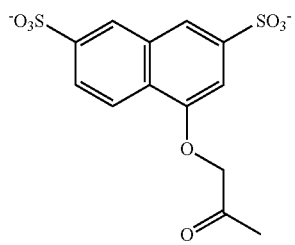

provided that at least one R group is a group of formula IV or a pharmaceutically acceptable salt thereof.

In particular embodiments, more than one R group is a group of formula IV, especially where at least 10 of the R groups are groups of formula IV, at least 15 of the R groups are groups of formula IV, at least 20 of the R groups are groups of formula IV, at least 25 of the R groups are groups of formula IV or at least 30 of the R groups are groups of formula IV. In some embodiments, all of the R groups are groups of formula IV.

A particular dendrimer of formula I has all R groups as groups of formula IV (SPL7013). A particular dendrimer of formula II has all R groups as groups of formula IV (SPL7320). A particular dendrimer of formula III has all R groups as groups of formula IV (SPL7304).

The synthesis of dendrimers of Formulae I, II and III is described in WO 02/079299.

The above macromolecules are known to have low toxicity and not be absorbed systemically when applied topically. In some embodiments of the present invention, the macromolecule has low toxicity and can be administered to eye with low or no irritation to the eye of the subject.

The macromolecule of the invention may be delivered in any formulation suitable for application to the eye, for example, solutions, ointments, gels, lotions, in slow release polymers or coated, on bound to or impregnated in contact lenses. By "suitable for application to the eye" is meant that any component of the formulation does not cause a long-lasting deleterious effect on the eye or the subject being treated. Transient effects such as minor irritation or "stinging" upon administration may occur without long-lasting deleterious effect. The macromolecule may be formulated as a simple aqueous solution. Alternatively, the macromolecule may be formulated to have one or more of physiologically compatible osmolality and pH, for example, by including salts and buffering agents, and other components such as preservatives, gelling agents, viscosity control agents, ophthalmic lubricating agents, mucoadhesive polymers, surfactants, antioxidants and the like in a solution, gel, lotion or ointment.

The macromolecules of the present invention are retained on or in the epithelium for a period of time, allowing the macromolecule to diffuse out of epithelium. Such diffusion provides slow release of drug into the ocular environment, enabling the anti-viral activity of the macromolecule to be delivered over a period and not be quickly washed away by the ocular fluids and physical cleansing. The macromolecule may be released from the epithelium over a period of greater than 10 minutes, more especially over a period greater than 1 hour, and more especially over a period of more than 6 hours.

In yet a further aspect of the invention there is provided a composition comprising a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer and at least one pharmaceutically acceptable carrier that provides pH and osmolality compatible with the eye.

Suitable ophthalmically acceptable salts that may be used as osmolality agents include salts having sodium, potassium or ammonium cations and chloride, citrate, ascorbate, borate, phosphate, bicarbonate, sulfate, thiosulfate or bisulfite ions. Examples of suitable salts include sodium chloride, potassium chloride, sodium thiosulfate, sodium bisulfate and ammonium sulfate.

Suitable ophthalmically acceptable pH adjusting agents and/or buffering agents include acids such as acetic, boric, citric, lactic, phosphoric and hydrochloric acids, bases such as sodium hydroxide, sodium phosphate, sodium borate, sodium citrate, sodium acetate, sodium lactate and trishydroxymethylaminomethane, and buffers such as citrate-dextrose, sodium bicarbonate and ammonium chloride.

Suitable preservatives include stabilized ammonium compounds such as benzalkonium chloride, cetyltrimethylammonium chloride and cetylpyridinium chloride, mucuric compounds such as phenyl mercuric acetate, imidazolidinyl urea, parabens such as methyl paraben, ethyl paraben, propyl paraben or butyl paraben; phenoxyethanol, chlorophenoxyethanol, phenoxypropanol, chlorobutanol, chlorocresol, phenylethyl alcohol, ethylenediamine tetraacetic acid, sorbic acid and salts thereof.

Suitable gelling agents or viscosity control agents include gelling agents that increase viscosity when they come into contact with lacrimal fluid, for example, lacrimation caused by blinking or tears. Such gelling agents may be used to reduce loss of the macromolecule by lacrimal drainage and allow the macromolecule to have increased residence time and therefore absorption in the eye or epithelial layer of the eyelids. Suitable gelling agents include gellan gum, especially low acetylated gellan gum, alginate gum or chitosan. The viscosity adjusting agent may also include a film-forming polymer such as an alkylcellulose such as methyl cellulose or ethylcellulose, a hydroxyalkylcellulose such as hydroxyethyl cellulose or hydroxypropyl methylcellulose, hyaluronic acid or its salts, chondroitin sulfate or its salts, polydextrose, cyclodextrin, polydextrin, maltodextrin, dextrin, gelatine, collagen, polygalacturonic acid derivatives such as pectin, natural gums such as xanthan, locust bean, acacia, tragacanth and carageenan, agar, polyvinyl alcohol, polyvinylpyrrolidone, polyethylene glycol, polymers of acrylamide, acrylic acid and polycyano acrylates and polymers of methylmethacrylate and 2-hydroxy-ethyl methacrylate. The viscosity control agent or gelling agent may be present in an amount of 0.1% to about 6.5% w/w of the composition, especially about 0.5% to 4.5% w/w of the composition.

Suitable lubricating agents include polyvinyl alcohol, methyl cellulose, hydroxypropyl methylcellulose and polyvinylpyrrolidone.

Suitable mucoadhesive polymers include hydroxypropyl methylcellulose, carboxymethylcellulose, poly(methylmethacrylate), polyacrylamide, polycarbophil, polyethylene oxide, sodium alginate and dextrin.

Suitable ophthalmically acceptable surfactants include non-ionic surfactants such as polyoxyethylene fatty acid glycerides and vegetable oils including polyoxyethylene

(60) hydrogenated castor oil, polyoxyethylene alkylethers and alkylphenyl ethers such as octoxynol 10 and octoxynol 40.

Suitable antioxidants include ascorbic acid and sodium metabisulfate.

Ophthalmic ointments may also include one or more of thickeners such as liquid paraffin, yellow soft paraffin, hard paraffin, and/or wool fat.

The macromolecule of the invention may be present in the formulation in an amount in the range of about 0.1% by weight to about 10% by weight, especially between 0.5% to 8% w/w or 1% to 5% w/w.

While it is possible that the composition of the invention may be formulated with carriers, diluents and excipients commonly used in the art as discussed above in topical eye formulations, it is well known that a number of commonly used preservatives have drawbacks when used in topical eye formulations. For example, some preservatives cause eye irritation and if used for long term therapy, they may cause damage to the eye. Furthermore, some preservatives are not effective against some strains of bacteria causing spoilage of the compositions. Examples include benzalkonium chloride, which is ineffective against some microbes such as strains of *P. aerugenosa* and *M. tuberculosis, T. rubrum* and *Trichophyton interdigitale*, and may be incompatible with buffers such as citrate and phosphate buffers. Furthermore benzalkonium chloride may be harmful to the eye and is not suitable for contact lens wash solutions as it causes ocular toxicity if used long term. Phenyl mercuric acetate cannot be used as a preservative in eye drop formulations to be used long term because mercurialentis may occur. Parabens are generally regarded as unsuitable for ophthalmic formulations because of their irritant nature. In some cases eye drop compositions are formulated without preservative to reduce irritancy. However, such formulations must be packaged for single use or refrigerated once they are opened.

The formulation of the present invention has the advantage that the macromolecule not only has antiviral and antimicrobial activity, but also has preservative activity. The composition of the invention may therefore be formulated without conventional preservatives and be stable at room temperature for storage.

In its most simple state, the formulation of the invention consists of an aqueous solution of the macromolecule together with at least one pharmaceutically acceptable excipient, wherein the at least one excipient provides a pH of 7.0 to 7.6 and osmolality of 240 to 310 mOsm/kg, especially an osmolality that is isotonic with tears. In other embodiments, the formulation comprises an aqueous solution of the macromolecule together with at least one pharmaceutically acceptable excipient, wherein the at least one excipient provides a pH of 7.0 to 7.5 and osmolality of 240 to 310 mOsm/kg but preservatives other than the macromolecule is excluded.

Contact lens wearers are particularly susceptible to conjunctivitis due to the insertion of foreign bodies in their eyes. The risk of conjunctivitis may be reduced by including a macromolecule of the present invention in contact lens solutions. Contact lens solutions include washing, rinsing, storing, disinfecting, rewetting, lubricating, general purpose solutions and concentrated medicinal solutions. The macromolecules of the present invention are retained on the contact lens and diffuse out of the lens and onto the eye to provide slow release into the ocular environment. The diffusion from the lens enables the anti-viral activity of the macromolecule to be delivered over a longer period of time than without the lens.

Therefore in another aspect of the invention there is provided a contact lens solution comprising a macromolecule or a pharmaceutically acceptable salt thereof comprising a dendrimer of 1 to 8 generations with one or more sulfonic acid- or sulfonate-containing moieties attached to one or more surface groups of the outermost generation of the dendrimer.

In some embodiments, the macromolecule may be present in an amount of 0.5% to 10% of the solution, especially, the macromolecule may be present in an amount of 1% to 5% of the solution, especially 1% to 5%, and more especially 1% to 3% of the solution. Where the solution is prepared as a concentrated additive, the macromolecule may be present in an amount of 5% to 25% of the solution, especially 10% to 20%.

The macromolecules of the present invention are retained on or in the contact lens for a period of time, allowing the macromolecule to diffuse out of the lens. Such diffusion provides slow release of drug into the ocular environment, enabling the anti-viral activity of the macromolecule to be delivered over a period and not be quickly washed away by the ocular fluids and physical cleansing. The macromolecule may be released from the contact lens over a period of greater than 10 minutes, more especially over a period greater than 1 hour, and more especially over a period of more than 6 hours The contact lens solution of the invention may also include other components such as buffers, isotonicity agents, demulcents, wetting agents, surfactants, chelating agents, enzymes, antiseptics, anaesthetics and optionally preservatives.

In some embodiments, the antiseptic is selected from polyhexamethylene biquanide (PHMB), N-alkyl-2-pyrrolidone, chlorhexidine, polyquaternium-1, hexetidine, bronopol, alexidine, low concentrations of hydrogen peroxide, and ophthalmologically acceptable salts thereof in an amount of 0.00001 to 0.01 or 0.00001 to 0.1 wt % of the composition.

Ophthalmologically acceptable chelating agents useful in the present invention include amino carboxylic acid compounds or water-soluble salts thereof, including ethylenediaminetetraacetic acid (EDTA), nitrilotriacetic acid, diethylenetriamine pentaacetic acid, hydroxyethylethylenediaminetriacetic acid, 1,2-diaminocyclohexanetetraacetic acid, ethylene glycol tetraacetic acid (EGTA), aminodiacetic acid and hydroxyethylamino diacetic acid. These acids can be used in the form of their water soluble salts, particularly their alkali metal salts. Especially preferred chelating agents are the di-, tri- and tetra-sodium salts of ethylenediaminetetraacetic acid (EDTA), most preferably disodium EDTA (disodium edetate).

Other chelating agents such as citrates and polyphosphates can also be used in the present invention. The citrates which can be used in the present invention include citric acid and its mono-, di-, and tri-alkaline metal salts. The polyphosphates which can be used include pyrophosphates, triphosphates, tetraphosphates, trimetaphosphates, tetrametaphosphates, as well as more highly condensed phosphates in the form of the neutral or acidic alkali metal salts such as the sodium and potassium salts as well as the ammonium salt.

The pH of the solution should be adjusted to be compatible with the eye and the contact lens such as between 6.0 to 8.0, preferably between 6.8 to 7.9 or between 7.0 to 7.6. Significant deviations from neutral will cause changes in the physical parameters (i.e. diameter) in some contact lenses.

Suitable tonicity agents include sodium chloride, potassium chloride, propylene glycol, glycerol or mixtures thereof. The tonicity of the solution is typically adjusted to approximately 240-310 milliosmoles per kilogram solution (mOsm/kg) to render the solution compatible with ocular tissue and with hydrophilic contact lenses. In one embodiment, the solution contains 0.01 to 0.5 weight percent sodium chloride.

Suitable viscosity inducing agents can include lecithin or the cellulose derivatives such as hydroxymethylcellulose, hydroxypropylcellulose, hydroxymethylethyl cellulose, and methylcellulose in amounts similar to those for surfactants, above.

In a further aspect of the invention, there is provided a microbicidal delivery system comprising a contact lens and a macromolecule or a pharmaceutically acceptable salt thereof comprising a dendrimer of 1 to 8 generations with one or more sulfonic acid- or sulfonate-containing moieties attached to one or more surface amino groups of the outermost generation of the dendrimer.

The present invention will now be more fully described with reference to the accompanying examples. It should be understood, however, that the description following is illustrative only and should not be taken in any way as a restriction on the generality of the invention described above.

EXAMPLES

Example 1: Anti-Adenoviral Activity—Prevention of Viral Penetration of Cells

The penetration of adenovirus into cells was assessed using a titer reduction assay (Hayashi, K: Characterization of antiviral activity of a sesquiterpene, triptofordin C-2, *J. Antimicrob. Chemother.*, 1996, 37(4). 759-68). Prevention of penetration of the virus into a cell measures the ability of the active agent to prevent cell penetration and consequently preclude infection.

Adenovirus subtype 5 (ATCC #VR-5) was used with HeLa cells (ATCC #CCL-2), Adenovirus subtype 8 (ATCC #VR-1640) was used with A549 cells (ATCC #CCL-185), Adenovirus subtype 19 (ATCC #VR-254) was used with Chang C cells (ATCC #CCL-20.2) and Adenovirus 37 (ATCC #VR-929) was used with WI-38 cells (ATCC #CCL-75). Both epithelial and fibroblast cell types were used.

Cells were incubated with different concentrations (10, 3, 0.5, 0.1, 0.02 0.004% w/v) of SPL7013 or no SPL7013, in serum free media for 60 minutes at 37° C. Following the incubation, aliquots of 0.1 MOI virus were inoculated and allowed to adsorb to cells for 1 hour at 4° C.±2° C. After incubation, free virus was removed by washing with Eagle's minimum essential medium with appropriate supplements for each cell line and incubated for approximately 30 minutes at 37° C. to allow for virus penetration. The cells were then trypsinized and virus which had penetrated was determined by titration as follows.

The recovered virus was titrated in the susceptible cell lines by performing dilutions at 1/10 to 1/100,000 and addition to cells in plates. When cytopathic effect (CPE) was apparent in the virus control, titration plates were classified as positive or negative for cytopathic effect and based on the dilution of the virus applied to the different plates, the 50% tissue-culture infective dose ($TCID_{50}$) was calculated using the Spearman-Kärber method (Hubert, J J (1984) Spearman-Karber Method in *Bioaasay*. Hunt, Dubuque, Iowa, pp 65, 66). The $TCID_{50}$ establishes the dilution at which 50% of the plates show a cytopathic effect (infection). Comparing the $TCID_{50}$ for sample without SPL7013 with the $TCID_{50}$ values for samples with different concentrations of SPL7013 provides a measure of the percent reduction of infection achieved by each concentration of SPL7013. This percent reduction represents the activity of SPL7013 against penetration of cells with adenoviruses.

A control substance (cidofovir) was tested alongside SPL7013 at 20 μg/mL, 2 μg/mL, 0.2 μg/mL and 0.02 μg/mL (Gordon Y J, *Antiviral Research*, 1991, 16(1), 11-16). Because cidofovir acts later in the viral replication cycle, target cells were first infected with 0.1 MOI virus and incubated 60 minutes at 37° C.±2° C. Virus was removed, cidofovir was added at the respective concentrations and cells were incubated until CPE reached its maximum. Cells were then lysed and virus was titrated as described above.

The following Table 1 lists the average percent reductions over two experiments achieved by SPL7013 against the different adenoviridiae at different concentrations of SPL7013. Table 2 lists the percent reductions achieved by the positive control (cidofovir).

TABLE 1

Percent reduction of adenoviral penetration in the presence of SPL7013

| | SPL7013 concentration (in %, w/v) | | | | | |
|---|---|---|---|---|---|---|
| Subtype | 10 | 3.0 | 0.5 | 0.1 | 0.02 | 0.004 |
| Adeno-5 | 99.58% | 98.67% | 98.22% | 82.22% | 25.01% | 0.00% |
| Adeno-8 | 95.78% | 97.63% | 92.5% | 90% | 82.22% | 68.38% |
| Adeno-19 | 99.68% | 99.44% | 36.84% | 94.38% | 90.0% | 76.29% |
| Adeno-37 | 99.93% | 99.76% | 99.58% | 96.84% | 43.77% | 25.01% |

TABLE 2

Percent reduction of adenoviral replication in the presence of cidofovir

| | cidofovir concentration (in μg/mL) | | | |
|---|---|---|---|---|
| Subtype | 20 | 2 | 0.2 | 0.02 |
| Adeno-5 | 90.00% | 86.66% | 82.22% | 68.38% |
| Adeno-8 | 99.00% | 98.67% | 98.22% | 90.00% |
| Adeno-19 | 94.38% | 43.77% | 0.00% | 0.00% |
| Adeno-37 | >99.99% | 99.99% | 57.83% | 0.00% |

$IC_{50}$ values were estimated for both SPL7013 and cidofovir and calculated on a molar basis. The molecular weight used for SPL7013 is 16582 g/mol and cidofovir 279 g/mol. Table 3 shows the estimated $IC_{50}$ values for both compounds.

TABLE 3

IC$_{50}$ values determined for SPL7013 and Cidofovir for four adenovirus subtypes

| Adenovirus strain | IC$_{50}$Cidofovir (µM) | IC$_{50}$ SPL7013 (µM) |
|---|---|---|
| Adeno-5 | 0.559 | 72.4 |
| Adeno-8 | 0.112 | 12.1 |
| Adeno-19 | 52.4 | 3.62 |
| Adeno-37 | 0.112 | 29.6 |

Testing showed that SPL7013 inhibited adenovirus penetration and therefore infection of the selected subtypes of adenovirus tested at concentrations at or above 0.02%. The maximum anti-infective activity was seen against adenovirus subtype 37 where inhibition of penetration of more than 99.5% was observed at concentrations of 0.5% and above.

Example 2: Anti-Adenoviral Activity—Virucidal Activity

For a virucidal assay (*Standard Test Method to Assess the Activity of Microbicides against Viruses in Suspension*, ASTM E 1052), SPL7013 was exposed to adenovirus subtypes at different concentrations (0.5%, 1.0%, 3.0% and 10.0% w/v) for different amounts of time (30 sec, 1 min, 5 min, 30 min, 1 hr). Only a few samples were tested at 30 sec. After exposure, SPL7013 was neutralized with foetal calf serum. This neutralized sample was then diluted 1/10 to 1/100,000. These dilutions were used to infect target cells (cells and virus details are as described for Example 1) in plates. After sufficient incubation (5-14 days at 37° C.±2° C.), plates were classified as positive or negative for cytopathic effect and based on the dilution of the virus applied to the different plates, the tissue-culture infective dose (TCID$_{50}$) was calculated (see Example 1 for the method). Comparing the TCID$_{50}$ for samples without SPL7013 with the TCID$_5$, values for samples with SPL7013 allows calculation of % virus killed by SPL7013. The results are shown in Table 4.

TABLE 4

Virucidal activity of SPL7013 against selected adenovirus subtypes (% virus killed)

| Virus | SPL7013 concentration | 30 secs | 1 min | 5 min | 30 min | 1 h |
|---|---|---|---|---|---|---|
| Adeno-5 | 0.5% (w/w) | 0.00% | 0.00% | 0.00% | 43.77% | 82.88% |
| Adeno-5 | 1.0% (w/w) | | 0.00% | 0.00% | 0.00% | 43.77% |
| Adeno-5 | 3.0% (w/w) | | 43.77% | 0.00% | 0.00% | 43.77% |
| Adeno-5 | 10.0% (w/w) | | 0.00% | 0.00% | 43.77% | 82.22% |
| Adeno-8 | 1.0% (w/w) | | 68.38% | 68.38% | 82.22% | 96.84% |
| Adeno-8 | 3.0% (w/w) | | 43.77% | 0.00% | 0.00% | 82.22% |
| Adeno-8 | 10.0% (w/w) | | 68.38% | 82.22% | 94.38% | 90.00% |
| Adeno-19 | 1.0% (w/w) | | 0.00% | 68.38% | 0.00% | 0.00% |
| Adeno-19 | 3.0% (w/w) | | 0.00% | 68.38% | 0.00% | 0.00% |
| Adeno-19 | 10.0% (w/w) | | 0.00% | 68.38% | 43.77% | 43.77% |
| Adeno-37 | 0.5% (w/w) | 68.38% | 0.00% | 43.77% | 68.38% | 68.38% |
| Adeno-37 | 1.0% (w/w) | | 0.00% | 43.77% | 43.77% | 43.77% |
| Adeno-37 | 3.0% (w/w) | 68.38% | 0.00% | 43.77% | 82.22% | 68.38% |
| Adeno-37 | 10.0% (w/w) | | 0.00% | 0.00% | 43.77% | 68.38% |

SPL7013 shows the ability to kill up to 96.84% of virus. The ability of SPL7013 to kill adenovirus in concert with its ability to inhibit penetration, provide evidence of the effectiveness of SPL7013 to treat and prevent adenoviral infections.

Example 3: Anti-Adenoviral Activity of Macromolecules

The anti-adenoviral activity of a selection of macromolecules was assessed by the following method.

For the Cytopathic assay (CPE) Plates of cells were incubated with the respective adenovirus subtype and drug at different drug concentrations. Cells were incubated until a Cytopathic effect was clearly observed in plates where cells and virus were plated without drug. In plates where drug was added, the cytopathic effect was quantified using a light microscope and expressed as 0% (no effect) up to 100% (effect as strong as in the no drug control plates). CPE readings were plotted against the drug concentration and the EC50 value was determined as the drug concentration where 50% CPE was observed.

The Plaque reduction neutralization test (NR) is used to quantify the ability of a dendrimer to neutralize/inactivate virus. The dendrimer solution to be tested is diluted and mixed with a viral suspension. This is incubated to allow the dendrimer to react with the virus. This is poured over a confluent monolayer of host cells. The surface of the cell layer is covered in a layer of agar or carboxymethyl cellulose to prevent the virus from spreading. The concentration of plaque forming units can be estimated by the number of plaques (regions of infected cells) formed after a few days. Depending on the virus, the plaque forming units are measured by microscopic observation, fluorescent labelled antibodies or specific dyes that react with infected cells. The concentration of dendrimer to reduce the number of plaques by 50% compared to the dendrimer free virus gives the EC50 value.

Ribivirin was included as a positive control. The results are shown in Table 5.

TABLE 5

Anti-adenoviral activity

| Test Compound | Dendrimer Type | Dendrimer Case | Dendrimer Generation | Adenovirus/ Protocol | $EC_{50}$ (µg/mL) |
|---|---|---|---|---|---|
| [BHALys][Lys]$_{16}$[CSNH-3,6-Naph(SO$_3$Na)$_2$]$_{32}$ | Lysine | BHALys | 4 | Adeno-5/CPE | 300 |
| [BHALys][Lys]$_{16}$[CSNH-3,6-Naph(SO$_3$Na)$_2$]$_{32}$ | Lysine | BHALys | 4 | Adeno-5/CPE | 70 |
| [NH$_3$][PAMAM]$_2$[CSNH-3,5-Ph(SO$_3$Na)$_2$]$_{24}$ | PAMAM | NH$_3$ | 4 | Adeno-5/NR | 150 |
| [NH$_3$][PAMAM]$_4$NHCSNH-2-naphth-5,7-(SO$_3$Na)$_2$]$_{24}$ | PAMAM | NH$_3$ | 4 | Adeno-1/CPE | 20 |
| [BHALys][Lys]$_{32}$deoxycholicacid[NHCSNH-4-ph-SO$_3$Na]$_{63}$ | Lys | BHALys | 5 | Adeno-1/CPE | 20 |
| [BHALys][Lys]$_{32}$deoxycholicacid[NHCSNH-4-ph-SO$_3$Na]$_{63}$ | Lys | BHALys | 5 | Adeno-1/NR | 10 |
| Ribavirin | — | — | — | NR | 10 |

Example 4: Virucidal Activity Against Herpes Virus

The virucidal activity of SPL7013 against herpes virus HSV-2 was assessed using the Test Method of the American Society for Testing and Materials to assess the activity of microbicides against viruses in suspension (ASTM E1052).

Virucidal activity of 0.5% SPL7013 (5 mg/mL) against HSV-2$_{MS}$ and 5% SPL7013 (50 mg/mL) against HSV-2$_G$.

The results for 0.5% SPL7013 are shown in Table 6A, (and corresponding controls in Table 6B) and for 5% SPL7013 are shown in Table 7.

TABLE 6A

| Dilution ($-Log_{10}$) | Exposure Time | | | | |
|---|---|---|---|---|---|
| | 30 seconds | 1 minutes | 5 minutes | 30 minutes | 60 minutes |
| −3 | ++++ | ++++ | 0+++ | 0+++ | 0++0 |
| −4 | ++++ | 0000 | 0000 | 0000 | 0000 |
| −5 | +000 | 0000 | 0000 | 0000 | 0000 |
| −6 | 0000 | 0000 | 0000 | 0000 | 0000 |
| −7 | 0000 | 0000 | 0000 | 0000 | 0000 |
| TCID50 (log10) | 4.75 | 3.50 | 3.25 | 3.25 | 3.00 |
| Log Reduction (log 10) | 2.001 | 3.00 | 3.50 | 3.50 | 3.50 |
| Average Percent Reduction | 99.00% | 99.90% | 99.97% | 99.97% | 99.97% |

TABLE 6B

| Dilution ($-Log_{10}$) | Virus Control | | | | | Neutralization Control | Cell Cytotoxicity | Cell Control |
|---|---|---|---|---|---|---|---|---|
| | 30 seconds | 1 minutes | 5 minutes | 30 minutes | 60 minutes | | | |
| −3 | ++++ | ++++ | ++++ | ++++ | ++++ | ++++ | 0000 | 0000 |
| −4 | ++++ | ++++ | ++++ | ++++ | ++++ | ++++ | 0000 | |
| −5 | ++++ | ++++ | ++++ | ++++ | ++++ | ++++ | | |
| −6 | ++++ | 0+++ | ++++ | 0+++ | ++++ | +++0 | | |
| −7 | +000 | 00+0 | 00+0 | 0+0+ | 0000 | 0000 | | |
| TCID50 (log 10) | 6.75 | 6.50 | 6.75 | 6.75 | 6.50 | 6.25 | | |

+ CPE present;
0 - CPE not detected;

TABLE 7

Herpes simplex virus type 2 + SPL7013 Batch 26-023-044-09
Exposure Time

| Dilution | 30 seconds | 1 minute | 5 minutes | 15 minutes | 30 minutes | 1 hour |
|---|---|---|---|---|---|---|
| Cell control | 0 0 0 0 | 0 0 0 0 | 0 0 0 0 | 0 0 0 0 | 0 0 0 0 | 0 0 0 0 |
| $10^{-2}$ | 0 0 0 0* | 0 0 0 0* | 0 0 0 0* | 0 0 0 0* | 0 0 0 0* | 0 0 0 0* |
| $10^{-3}$ | 0 0 0 0* | 0 0 0 0* | 0 0 0 0* | 0 0 0 0* | 0 0 0 0* | 0 0 0 0* |
| $10^{-4}$ | 0 0 0 0* | 0 0 + 0* | 0 0 0 0* | 0 0 0 0* | 0 0 0 0* | 0 0 0 0* |
| $10^{-5}$ | + + + + | + + + + | + + + + | 0 + + 0 | 0 0 0 0 | 0 0 0 0 |
| $10^{-6}$ | + 0 + 0 | 0 0 0 0 | + 0 0 0 | + + 0 0 | 0 0 0 0 | 0 0 0 0 |

TABLE 7-continued

Herpes simplex virus type 2 + SPL7013 Batch 26-023-044-09

| | Exposure Time | | | | | |
|---|---|---|---|---|---|---|
| Dilution | 30 seconds | 1 minute | 5 minutes | 15 minutes | 30 minutes | 1 hour |
| $10^{-7}$ | 0 0 0 0 | 0 0 0 0 | 0 0 0 0 | 0 0 0 0 | 0 0 0 0 | 0 0 0 0 |
| $TCID_{50}/0.1$ mL | $10^{6.0}$ | $10^{5.5}$ | $10^{5.75}$ | $10^{5.5}$ | **$\leq 10^{3.5}$ | **$\leq 10^{3.5}$ |
| Percent Reduction | No Reduction | 68.4% | 43.8% | 82.2% | $\geq$99.9% | $\geq$99.7% |
| $Log_{10}$ Reduction | No Reduction | 0.5 $Log_{10}$ | 0.25 $Log_{10}$ | 0.75 $Log_{10}$ | $\geq$3.0 $Log_{10}$ | $\geq$2.5 $Log_{10}$ |

+ = Positive for the presence of test virus
0 = No test virus recovered and/or no cytotoxicity present
\* = Cells appear fixed
\*\* = $TCID_{50}/0.1$ mL results based on the neutralization control result Example 5: Antibacterial Activity—Preservative Efficacy Test To assess the anti-microbial properties of a solution of aqueous SPL7013, two aqueous solutions were prepared, one at 5% w/v, and the second at 28% w/v. Standard preservative effectiveness tests (according to USP <51>"Antimicrobial Effectiveness Test") were conducted in order to challenge the capacity of each solution to limit microbial growth over a one month period.

5% and 28% w/w SPL7013 Solution

SPL7013 was prepared as either a 5% or 28% w/w solution in water, with the sample agitated to facilitate dissolution.

Test Method

The solutions were challenged with the following microbial organisms:

Pseudomonas aeruginosa, ATCC 9027
Staphycocccus aureus, ATCC 6538
Candida albicans, ATCC 10231
Aspergillus niger, ATCC 16404
Escherichia coli, ATCC 8739

Test inoculum is added to each sample such that the final concentration after inoculation is between $1 \times 10^5$ and $1 \times 10^6$ cfu per mL of product (as determined by the plate-count method). The inoculated containers are incubated at 22.5±2.5° C. and sampled after 14 and 28 days. On sampling, the concentration of each microorganism is determined by the plate-count method.

TABLE 8

$Log_{10}$ reduction of organisms after exposure to SPL7013

| | Initial | Final Count/cfu per g | | | |
|---|---|---|---|---|---|
| | Count/ | 5% w/v solution | | 28% w/v solution | |
| Organism | cfu per g | 14 days | 28 days | 14 days | 28 days |
| P. aeruginosa | $1.0 \times 10^6$ | <10 | <10 | <10 | <10 |
| S. aureus | $8.6 \times 10^5$ | <10 | <10 | <10 | <10 |
| C. albicans | $1.3 \times 10^6$ | $6.6 \times 10^5$ | $4.5 \times 10^5$ | $7.3 \times 10^4$ | 340 |
| A. niger | $8.0 \times 10^5$ | $7.0 \times 10^5$ | $4.1 \times 10^5$ | $1.0 \times 10^6$ | $8.9 \times 10^5$ |
| E. Coli | $7.9 \times 10^5$ | 15 (est) | 25 (est) | <10 | <10 |

As shown in Table 8, the 5% w/v solution of SPL7013 acted as a bacteriocide against *Pseudomonas aeruginosa*, *Staphylococcus aureus* and *Escherichia coli* over a 14 day period, with no subsequent increase in microorganism concentration observed after 28 days. The same test solution demonstrated a static effect with respect to the *Candida albicans* and *Aspergillus niger* inoculums after 14 days.

As further shown in Table 6, the 28% w/v solution of SPL7013 acted as a bactericide against *Pseudomonas aeruginosa*, *Staphylococcus aureus* and *Escherichia coli* over a 14 day period, and also against *Candida albicans* over 28 days. The same test solution prevented growth of the *Aspergillus niger* inoculum over the duration of the test.

The antibacterial properties of the two test solutions (5% and 28% w/v SPL7013 in water) both meet the pass criteria of the test as preservatives in topical preparations.

Example 6: Binding of SPL7013 to Epithelial Tissue

To test the retention of SPL7013 to epithelial tissue exposed to fluid, SPL7013 was applied to a small film of tissue consisting of multiple stratified layers of epithelial cells, under a layer of fluid.

Two different formulations were tested in this experiment: SPL7013 at 30 mg/mL and 5 mg/mL in PBS, and SPL7013 gel (0.5% or 5 mg/mL) formulated with Lubrajel Fluid (United Guardian, Inc.). One epithelial tissue kit was used (MatTek Corporation, Cat# VEC-100-FT) and the tissues were dosed/prepared as outlined in Table 9.

TABLE 9

Dosing regimen for the multidose treatment

| Treatment | No of tissues | Concentration* | Matrix | Amount added | Incubation |
|---|---|---|---|---|---|
| Dosed | 3 | 30 mg/mL | PBS | 100 μL | 4 h at 37° C. |
| Dosed | 3 | 5 mg/mL | PBS | 100 μL | 4 h at 37° C. |
| Dosed | 3 | 5 mg/g | Lubrajel | 100 μL | 4 h at 37° C. |

*The concentration refers to SPL7013 in the respective dosing/spiking solution

Tissues were initially treated by placing into 6-well plates containing 0.9 mL of specific media and incubating over night at 37° C. Media was exchanged with 0.9 mL fresh media prior to dosing.

Tissues to be dosed were taken out of the incubator and 100 μL of the dosing solution was applied. Tissues were returned to the incubator and incubated for the prescribed amount of time. Tissues were then removed from the incubator and any remaining dosing solution was recovered and transferred into pre-labelled 1.5 mL centrifuge tubes. The tissue was then subjected a stringent wash protocol where tissues were initially washed under a stream of PBS 15 times followed by dipping into PBS and drying on paper tissue.

Tissues were then lysed using the Thermo-Scientific lysis kit (Tissue lysis kit; Thermo Scientific, Cat#78833). Briefly, 100 μL CER I reagent was added to each tissue. Then, using the tissue was homogenized by repeatedly pipetting it up and down. Then the tissue vortexed for 15 seconds, 10 minute incubation, addition of 5.5 µL CER II reagent, vortexing, incubation again for 1 minute, vortexed, centrifugation at 16,000×g for 5 minutes and finally transfer of the lysate to a fresh 1.5 mL tube.

All lysates were analysed by micellar electrokinetic chromatography under basic pH conditions. The method has previously been used for analysis of pharmacokinetic samples from clinical trial studies (Chen et al, *JAIDS,* 2009, 50(4), 375-380).

To account for blank plastic binding, a control experiment was performed where 15 naked tissue culture inserts were dosed identically to the 5 dosing protocols shown in Table 9. Each dose was performed in triplicate.

Table 10 shows the results of both the tissue and the blank binding test:

TABLE 10

SPL7013 recoveries from multidose treatment of tissues and control inserts

| SPL7013 | | | Recovered SPL7013 (µg) | | Recovered SPL7013 (%) | |
|---|---|---|---|---|---|---|
| Dose | Matrix | Time# | Tissue | Blank | Tissue | Blank |
| 0.5% | PBS | 4 h | 10.45 ± 2.97 | 0.7 ± 0.26 | 4.18 ± 1.19 | 0.28 ± 0.10 |
| 3% | PBS | 4 h | 92.57 ± 13.51 | 6.59 ± 3.59 | 6.17 ± 0.90 | 0.44 ± 0.24 |
| 0.5% | Lubrajel | 4 h | 9.06 ± 2.31 | 1.00 ± 0.69 | 2.91 ± 0.74 | 0.32 ± 0.22 |

The results are the mean ± standard deviation for three tissues used with each dosing solution.
Incubation was carried out at 37° C. in a humidified incubator with 5% $CO_2$ A blank binding test was performed in parallel to determine the amount of SPL7013 retained by the plastic vial alone. A small fraction of the dosed amount of SPL7013 (<0.5%) was retained by the tissue culture insert alone.

Significantly more SPL7013 was retained on tissues dosed with 3% SPL-7013 in PBS. These results suggest that SPL7013 is either able to bind strongly to the surface of the epithelial cells (without being washed away) or is able to penetrate into the upper layers of the epithelial cells. These experiments cannot differentiate whether all binding occurs at the surface only or how successful and how deep SPL7013 penetrates the tissues. Previous results have shown that SPL7013 can cross a monolayer of apical-basolateral polarised cells. Approximately 1-6% of applied SPL7013 was able to cross the layer and the basolaterally recovered SPL7013 was unexpectedly still active as an infectious agent.

Taken together, the results described here show that SPL7013 possesses the ability to penetrate tissue to a degree where 5% of dosed compound moves into the uppermost layers of the epithelium presumably via adhesion to the surface of epithelial cells and and/or diffusion into interstitial spaces proximal to the tissue surface. Host-pathogen interactions often take place in this location, hence the ability of some SPL7013 to infiltrate the upper epithelium is likely to enhance the compounds utility.

These data also support the lack of systemic absorption of SPL7013 observed in all non-clinical and clinical studies to date. For systemic absorption to occur the drug would need to penetrate substantially thicker layers of tissue than that studied here. It is assumed that the amount of SPL7013 present decreases significantly with increased tissue thickness and that none or very little penetrate sufficiently to make contact with circulatory vessels required for systemic absorption.

The tissue model consists of a small film of tissue consisting of multiple layers of epithelial cells to mimic epithelial tissue. This tissue is at the bottom of a small plastic well above which rests a layer of fluid (i.e. media). These binding studies have shown that SPL7013 is retained by the tissue, via adhesion to the surface of epithelial cells and and/or diffusion into interstitial spaces proximal to the tissue surface.

Example 7: Binding of SPL7013 to Contact Lenses

Experiments were conducted to assess the ability of SPL7013 to adhere to contact lenses to extend the period of delivery of SPL7013 to the eye, and reduce or prevent infection on or adjacent to the lens.

Test Procedure for Each Lens

Five rinse beakers were prepared with 50 mL Milli Q water, together with a smaller beaker with 15 mL Milli Q water (extraction beaker). The contact lens was rinsed with Milli Q water and allowed to air dry briefly. Any residual droplets were gently tapped off on the side of a beaker. The lens was then placed in a separate test beaker in a concave way (i.e. the edges sticking upwards). 1 mL of 10% SP7013 in water was placed on top of the lens and the solution incubated for 20 min or 60 min in the Test Solution.

The lens was rinsed by picking up the lens with tweezers and dropping the lens in the first rinsing vessel. The vessel was agitated with the tweezers for 5 seconds making sure that the tweezers were also rinsed. The above step was repeated in the second rinsing vessel. A total of 5 rinses were completed.

Release of Bound Material:

The lens was then dropped into the extraction beaker (with 15 mL) Milli Q water and sonicated for 10 min to free any bound SPL7013.

Preparation of Samples:

The sonicated solution was transferred into a 20 mL volumetric flask and filled to mark with water. A 1.5 mL sample was filtered into a HPLC vial. This is the "released" sample.

The residual Test Solution was transferred into a 500 mL volumetric flask and filled to mark with water and mixed. If no binding occurred the concentration in the 500 mL flask would be 0.2 mg/mL. The solution was diluted to 20 mL with water. This is the "unbound" sample.

All of the rinse solutions were poured into one 250 mL volumetric flask which was then filled to mark with water and mixed. This is the "rinse" sample.

Analysis:

HPLC analysis was conducted on the released and unbound and rinse samples run in duplicate and calibrated to samples of a 0.05 mg/mL stock solution of SPL7013. The mean peak area of the samples was calculated and the concentration of SPL7013 in the samples was calculated by the formula:

C(sample)=Area(sample)/Area(standard)×concentration of standard

The amount of SPL7013 released was calculated: m (released)=c (released sample)×20 mL and the amount of SPL7013 unbound was calculated: m (unbound)=c (unbound sample)×2000 mL. The amount of SPL7013 in the rinse fractions was calculated as m (rinse)=c (rinse)×250 mL.

The results are shown in Table 11

TABLE 11

| Experiment | Brand | Rinse Medium | Incubation time (min) | Applied SPL7013 (mg) | Rinse + Unbound (mg) | Released (mg) |
|---|---|---|---|---|---|---|
| Exp 1 (average of 2 experiments) | Bausch & Lomb Soft Lens (alphafilcon A) | Milli-Q | 20 | 100 | 83.25 | 0.28 |
| Exp 3 (1 hr Incubation) | Bausch & Lomb Soft Lens (alphafilcon A) | Milli-Q | 60 | 100 | 90.50 | 0.70 |
| Exp 4 (PBS rinse) | Bausch & Lomb Soft Lens (alphafilcon A) | PBS | 20 | 100 | 96.16 | 0.17 |
| Exp 5 (Different lens material) | Cooper Vision (omafilcon A 40%, Water 60%) | Milli-Q | 20 | 100 | 95.42 | 0.14 |

As shown above, the contact lenses tested retained SPL7013, which was subsequently released by a short sonication. The sonication step models the abrasion of the eye, as well as the time spent in the eye, and demonstrated that SPL-7013 can be released once bound to the lens. It is anticipated that the bound SPL7013 would gradually diffuse off the lens and onto the eye.

Example 8: Development of Bacterial Resistance to SPL7013

The potential for resistance to emerge after repeated exposure of target pathogens to sub-inhibitory concentrations of SPL7013 and other comparator agents was evaluated by serial passage. In addition, select mutants (isolates with MIC values ≥4-fold higher than the parental strain) were characterized by confirmatory MIC testing, evaluation of the stability of the mutant after drug-free passage, and determination of co-resistance patterns.

Materials and Methods
Test Articles

| Drug | Source | Catalog No. | Lot Number | Solvent |
|---|---|---|---|---|
| SPL7013 | Starpharma | | 26-023-044-09 | BHI + 3% Horse Serum |
| Clindamycin | Sigma | C5269 | 021M1533V | Water |
| Metronidazole | Sigma | M3761 | 095K0693 | 50% DMSO |
| Rifaximin | Fluka | 33999 | SZBB035XV | 50% DMSO |

All drugs were tested over a broad concentration range (128-0.002 mg/mL) based on the expected activity of the agents against the tested organisms and to allow for observation of increasing MICs during the course of the assay.

For selected mutants, co-resistance was determined to the antibiotics shown below:

| Drug | Source | Catalog No. | Lot Number | Solvent |
|---|---|---|---|---|
| Penicillin | Sigma | P3032 | 071M0740V | Water |
| Chloramphenicol | Sigma | C0378 | 100M0061V | 95% ETOH/Water |
| Tetracycline | Sigma | T3383 | 11M1693V | Water |
| Gentamycin | Sigma | G3632 | 097K06887 | Water |

Organisms

The test organisms consisted of ATCC organisms or representative clinical isolates:
  *Gardnerella vaginalis* ATCC 14018 (MMX 4153)
  *Prevotella bivia* MMX 3447
  *Mobiluncus curtisii* ATCC 35241 (MMX 4145)
  *Lactobacillus acidophilus* MMX 5716
  *Bacteroides fragilis* ATCC 25285 (MMX 0123) and *G. vaginalis* ATCC 14018 (MMX 4153) served as the quality control organisms tested in this study.

Isolates were sub-cultured on supplemented *Brucella* agar plates (Remel; Lenexa, Kans.; Catalog No. R01255; Lot Nos. 146893, 174114, 164387) and incubated anaerobically at 35° C. for 48 hr. Selected mutants were evaluated for stability after drug-free passage by subculturing three times over drug free supplemented *Brucella* agar plates.

Test Media

For all organisms, the MIC assay plate and growth medium was Brain Heart Infusion broth (BHI; Becton Dickinson, Sparks, Md.) supplemented with 3% Horse Serum (Cleveland Scientific; Bath, Ohio).

MIC Assay Methodology

MIC values were obtained for all isolates and test agents using the CLSI broth dilution method (Clinical and Laboratory Standards Institute, CLSI document M11-A7) with the exception that BHI containing 3% horse serum was used as the growth medium in place of supplemented *Brucella* broth.

For the comparator drugs, wells in columns 2-12 in a standard %-well microdilution plate were filled with 90 μL of drug solution at the appropriate dilution.

A standardized inoculum of each organism was prepared per CLSI methods (Clinical and Laboratory Standards Institute, CLSI document M11-A7). The plates were inoculated with 10 μL of standardized inoculum under anaerobic conditions to yield a final cell concentration of approximately $5 \times 10^5$ cfu/mL.

Plates incubated at 35° C. for 46 to 48 hr. The MIC was recorded as the lowest concentration of drug that inhibited visible growth of the organism.

Serial Passage Resistance Development

The contents of wells containing the highest concentration of drug in which there was growth were plated onto *Brucella* agar and incubated anaerobically for 48 hr at 35° C. The inoculum for the next passage was prepared by using growth from this agar plate. If the well at the highest sub-inhibitory concentration was judged to contain only marginal growth, contents from the well one dilution lower were also streaked onto Brucella agar to ensure that a fresh inoculum of sufficient density could be prepared for the next passage. From the plate, a 0.5 McFarland suspension was made and test plates were inoculated in accordance with CLSI (Clinical and Laboratory Standards Institute, CLSI document M11-A7). Fresh inocula of B. fragilis 0123 and G. vaginalis 4153 from frozen stocks were tested each day for the purposes of quality control.

The entire process was repeated through 10 serial passages. Passage 1 defined the baseline value for each organism. A significant change in MIC value was defined as a 4-fold increase from baseline value.

Results and Discussion

Against B. fragilis, 100% of metronidazole MICs were within range, and clindamycin MICs were within range with the exception of three days when the MIC was one well below the acceptable range. SPL7013 had no activity over the concentration range evaluated against B. fragilis, with MICs>128 mg/mL. Against G. vaginalis ATCC 14018, a proposed QC strain for SPL7013, the MICs of SPL7013 during serial passage were within the proposed range of 0.25-1 mg/mL with the exception of three test days when the MIC was one well above the proposed range.

Serial Passage

During serial passage of G. vaginalis ATCC 14018 (MMX 4153). MICs for SPL7013, metronidazole, and rifaximin increased several-fold above the MICs observed at baseline. By passage 9, the SPL7013 MIC had increased from 1 to 64 mg/mL (64-fold), while for metronidazole the MIC increased from 4 to >128 µg/mL (>64-fold) by passage 7. Rifaximin MICs increased from 0.06 to 128 µg/mL (>2000 fold) by passage 9. In contrast, no increase in MIC was apparent with clindamycin during passage.

Similar results were observed with M. curtisii ATCC 35241 (MMX 4145) when passaged, with the exception that resistance development to rifaximin was not apparent. SPL7013 MICs increased from 8 to 128 mg/mL (16-fold) by passage 9 while metronidazole MICs increased from 8 to >128 µg/mL (>16-fold) by passage 5. No apparent increase in rifaximin or clindamycin MICs were observed during passage.

For L. acidophilus MMX 5716, SPL7013 MICs increased 8-fold from 2 to 16 mg/mL by passage 4 while for rifaximin MICs increased 64-fold from 1 to 64 µg/mL by passage 9. Clindamycin MICs remained unchanged during passage.

During passage of P. bivia MMX 3447, the organism did not remain viable beyond passage 5. Through passage 5, no increase beyond 2-fold of the baseline MIC was observed for SPL7013 or metronidazole. For rifaximin, MICs increased 4-fold by passage from 0.03 to 0.12☐ µg/mL.

SUMMARY

In summary, there were some increases in SPL7013 MICs during serial passage with target bacterial pathogens and for L. acidophilus. Increases in MICs were also apparent among these organisms with metronidazole and rifaximin, and were often greater in magnitude and were earlier to develop than those observed with SPL7013. No resistance was apparent to clindamycin during serial passage.

With the exception of M. curtisii, the increases in SPL7013 MICs were confirmed upon retesting of the MIC and appeared to be stable as they remained elevated after drug free passage. Rifaximin and metronidazole mutants were also stable after drug-free passage. Upon evaluation of putative M. curtisii mutants, MICs for rifaximin and SPL7013 observed during serial passage were not confirmed during MIC retesting. This result suggests that M. curtisii mutants were not generated during serial passage with either SPL7013 or rifaximin, and for SPL7013 this appears to be due in part to an artificially low MIC observed at baseline and during early passage. In contrast, M. curtisii mutants to metronidazole did emerge during serial passage and were stable.

No co-resistance of SPL7013 derived mutants was evident across the evaluated comparator agents, indicating that decreased susceptibility to SPL7013 did not affect the activity of agents which target known, well-characterized pathways within bacteria.

Example 9: In Vivo Treatment of Adenoviral Infection

Following general anesthesia and corneal scarification, NZW female rabbits were inoculated in each eye with 50 µl of $3.0 \times 10^7$ PFU/mL ($1.5 \times 10^6$ PFU/eye) of Ad5 McEwen. At about 3 hours after inoculation, a swab was taken of the tear film and corneal and conjunctival surfaces into tubes containing 1 mL of outgrowth media, and cultured for adenovirus.

The rabbits were then divided into 3 groups: 3% SPL7013 (n=5), Vehicle (n=5) and 0.5% cidofovir in saline as positive control (n=4). Commencing on day 1, animals were treated in each eye with 37 µL of drug 8 times a day, or 37 µL of control twice a day. Swabs of the tear film and corneal and conjunctival surfaces were taken one hour after treatment.

Antiviral Tolerability:

At day 3, all eyes were evaluated for ocular tolerability of formulations using the Draize scoring method (Draize, J. H., Woodward, G. and Calvery, H. O. Methods for the study of irritation and toxicity of articles applied topically to the skin and mucous membranes. J. Pharmacol. Exp. Ther. 1944; 82:377-390.). and interpreted using Maximum Mean Total score (Kay J H, Calandra J C. Interpretation of eye irritation tests. J Soc Cos Chem. 1962; 13:281-289). All 3 groups scored as Minimally Irritating.

In conclusion, SPL7013 does not show significant ocular toxicity. The macromolecule has low toxicity and can be administered to the eye with low or no irritation.

Antiviral Efficacy:

Ad5 titers were determined on A549 lung carcinoma cell monolayers using a standard plaque assay. The ocular cultures were diluted and inoculated onto A549 monolayers, and the virus adsorbed for 3 hours. Following adsorption, 1 mL of media plus 0.5% methylcellulose was added to each well, and the plates were incubated at 37° C. in a 5% $CO_2$-water vapor atmosphere for 7 days, then stained with 0.5% gentian violet, and plaques were counted.

TABLE 12

| PFU of Ad5 | | | | |
|---|---|---|---|---|
| | % Ad5 -Positive cultures (n = 8-10) | | | |
| | Day 0 | Day 1 | Day 3 | Day 4 |
| 3% SPL7013 | 100% | 80% | 80% | 60% |
| Vehicle | 100% | 90% | 100% | 100% |
| 0.5% Cidofovir | 100% | 100% | 100% | 75% |

SPL7013 acts earlier than cidofovir, within 8 hours of receiving the first dose, and is more effective than cidofovir at reducing viral titer.

What is claimed is:

1. A method of treating or reducing a likelihood of an occurrence of a microbial infection in an eye of a subject comprising topically administering to the eye an effective amount of a macromolecule or a pharmaceutically acceptable salt thereof comprising a dendrimer selected from the group consisting of polylysine, polyglutamate, polyaspartate, polyamidoamine (PAMAM), poly(etherhydroxylamine), polyether, polyester or poly(propyleneimide) (PPI) having a core, 3 or 4 generations of monomeric building units, and a sulfonic acid- or sulfonate-containing moiety attached to each of the surface groups of an outermost generation of the dendrimer, wherein the sulfonic acid-containing moiety is selected from the group consisting of:

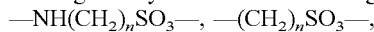

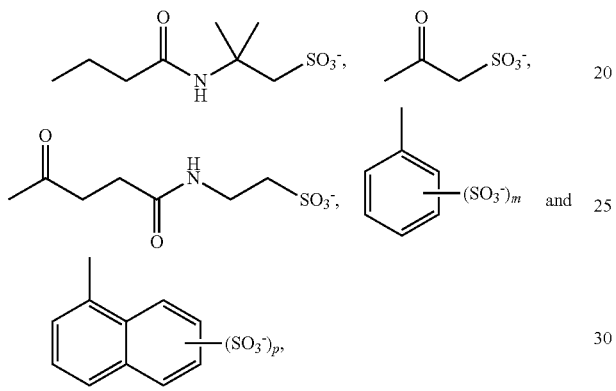

wherein n is zero or is an integer from 1-20, m is an integer 1 or 2 and p is an integer 1 to 3.

2. The method according to claim 1, wherein the microbial infection causes conjunctivitis.

3. A method according to claim 1 wherein the microbial infection is caused by adenovirus subtype 11, 8, 19, 37, 53, 54, 56 or 64.

4. The method according claim 2, wherein the conjunctivitis is selected from the group consisting of viral conjunctivitis, bacterial conjunctivitis, epidemic keratoconjunctivitis, acute epidemic conjunctivitis, pharyngoconjunctival fever, pinkeye, keratoconjunctivitis, swimming pool conjunctivitis, granular conjunctivitis and acute hemorrhagic conjunctivitis.

5. The method according to claim 1, wherein the subject is human.

6. The method according to claim 5 wherein the human is or has been wearing contact lens.

7. The method according to claim 1, wherein the macromolecule or a pharmaceutically acceptable salt is administered for more than 7 days.

8. The method according to claim 1, wherein said treating comprises alleviating, reducing or halting the progression of one or more symptoms of the microbial infection.

9. The method according to claim 8, wherein the symptom is one or more of eye redness, itchiness, irritation, photophobia, pain, vision impairment, swelling, watery eyes and discharge.

10. The method according to claim 1, wherein the microbial infection comprises one or more selected from the group consisting of a viral infection, a bacterial infection, a concurrent or undifferentiated viral and/or bacterial infection.

11. The method according to claim 10, wherein the viral infection is caused by a virus selected from the group consisting of adenovirus and herpes virus and the bacterial infection is caused by a bacteria selected from *Neisseria* spp., *Chlamydia* spp., *Staphylococcus* spp., *Streptococcus* spp., *Pseudomonas* spp. and *Haemophilus* spp.

12. The method according to claim 1, wherein the subject has the microbial infection in a first eye and the method comprises:
topically administering to a second eye of the subject an effective amount of a macromolecule or a pharmaceutically acceptable salt thereof comprising a dendrimer having a core, 3 or 4 generations of monomeric building units, and a sulfonic acid- or sulfonate-containing moiety attached to each of the surface groups of an outermost generation of the dendrimer so as to reduce a likelihood of occurrence of the microbial infection on the second eye.

13. The method according to claim 1, wherein the subject comprises a pregnant mother and the method comprises:
administering to a birth canal of the pregnant mother, a topical formulation comprising an effective amount of a macromolecule or a pharmaceutically acceptable salt thereof comprising a dendrimer having a core, 3 or 4 generations of monomeric building units, and a sulfonic acid- or sulfonate-containing moiety attached to each of the surface groups of an outermost generation of the dendrimer so as to reduce a likelihood of transmission of the microbial infection to an eye of a neonate during passage through the birth canal of its mother.

14. A composition for treating or reducing a likelihood of occurrence or symptoms of a microbial infection in an eye of a subject, said composition comprising a macromolecule or a pharmaceutically acceptable salt thereof comprising a dendrimer selected from the group consisting of polylysine, polyglutamate, polyaspartate, polyamidoamine (PAMAM), poly(etherhydroxylamine), polyether, polyester or poly(propyleneimide) (PPI) having a core, 3 or 4 generations of monomeric building units, and a sulfonic acid- or sulfonate-containing moiety attached to each of the surface groups of an outermost generation of the dendrimer, wherein the sulfonic acid-containing moiety is selected from the group consisting of:

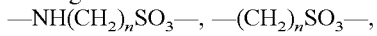

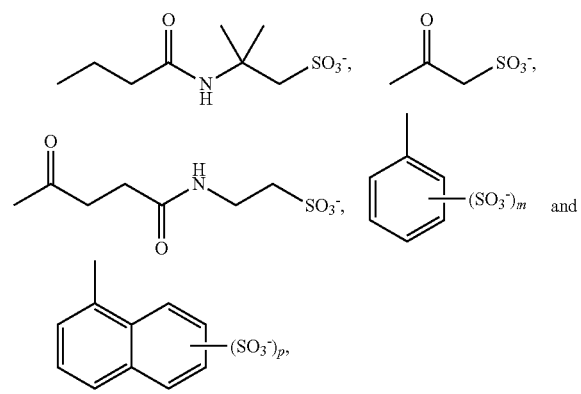

wherein n is zero or is an integer from 1-20, m is an integer 1 or 2 and p is an integer 1 to 3.

15. The composition according to claim 14 wherein the composition does not include a further preservative.

16. A contact lens solution comprising a macromolecule or a pharmaceutically acceptable salt thereof comprising a dendrimer selected from the group consisting of polylysine, polyglutamate, polyaspartate, polyamidoamine (PAMAM), poly(etherhydroxylamine), polyether, polyester or poly(propyleneimine) (PPI) having a core, 3 or 4 generations of monomeric building units, and a sulfonic acid- or sulfonate-containing moiety attached to each of the surface amino groups of an outermost generation of the dendrimer, wherein the sulfonic acid-containing moiety is selected from the group consisting of:

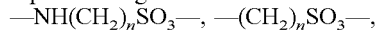

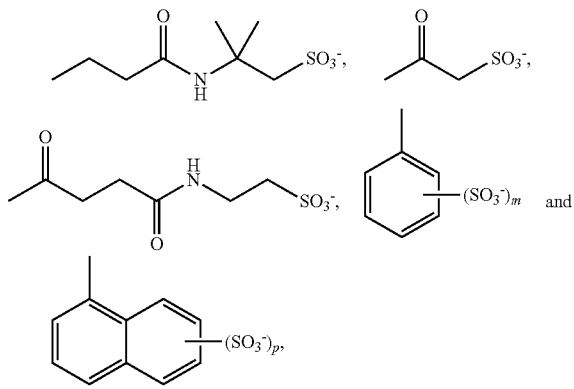

wherein n is zero or is an integer from 1-20, m is an integer 1 or 2 and p is an integer 1 to 3.

17. The composition according to claim 14, further comprising at least one pharmaceutically acceptable carrier that provides pH and osmolality compatible with the eye.

18. The composition according to claim 14 wherein the microbial infection causes conjunctivitis.

19. The composition according to claim 14 wherein the microbial infection is caused by adenovirus subtype 11, 8, 19, 37, 53, 54, 56 or 64.

20. The composition according to claim 18 wherein the conjunctivitis is selected from the group consisting of viral conjunctivitis, bacterial conjunctivitis, epidemic keratoconjuctivitis, acute epidemic conjunctivitis, pharyngoconjunctival fever, pinkeye, keratoconjunctivitis, swimming pool conjunctivitis, granular conjunctivitis and acute hemorrhagic conjunctivitis.

21. The composition according to claim 14 wherein the subject comprises a human who is or has been wearing contact lens.

22. The solution according to claim 16 wherein the solution treats or reduces a likelihood of an occurrence of a microbial infection.

23. The solution according to claim 22 wherein the microbial infection is caused by adenovirus subtype 11, 8, 19, 37, 53, 54, 56 or 64.

24. The method according to claim 1 where in the macromolecule or pharmaceutically acceptable salt thereof is administered 4 to 8 times per day.

25. The method according to claim 8 where in the macromolecule or pharmaceutically acceptable salt thereof is administered 4 to 8 times per day.

26. The composition according to claim 14, wherein the microbial infection is selected from the group consisting of adenovirus, herpes virus, *Neisseria* spp., *Chlamydia* spp., *Staphylococcus* spp., *Streptococcus* spp., *Pseudomonas* spp. and *Haemophilus* spp.

27. The composition according to claim 14, wherein the macromolecule or pharmaceutically acceptable salt thereof is at 1% w/w to 3% w/w.

28. The method according to claim 1, wherein the effective amount of the macromolecule or pharmaceutically acceptable salt thereof is 0.5 mg to 2.5 mg per dose.

29. The method according to claim 1, wherein the sulfonic acid-containing moiety is selected from the group consisting of:

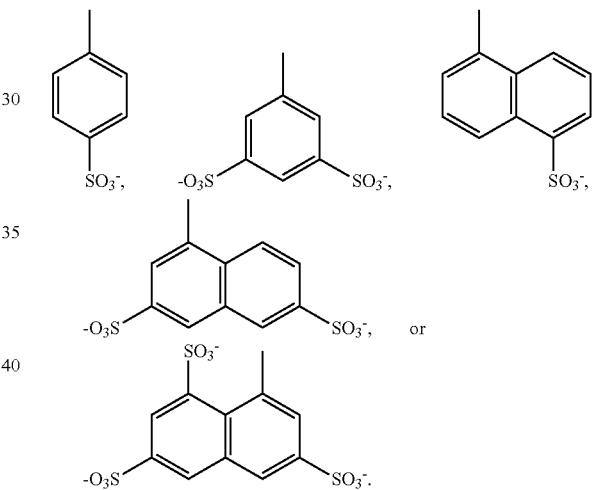

30. The method according to claim 1, wherein the dendrimer comprises lysine building units.

31. The method according to claim 1, wherein the dendrimer is

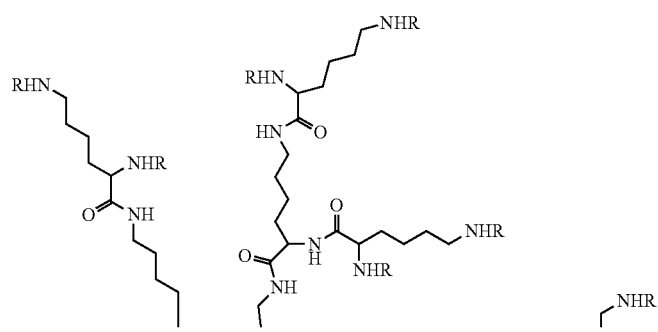

I

-continued
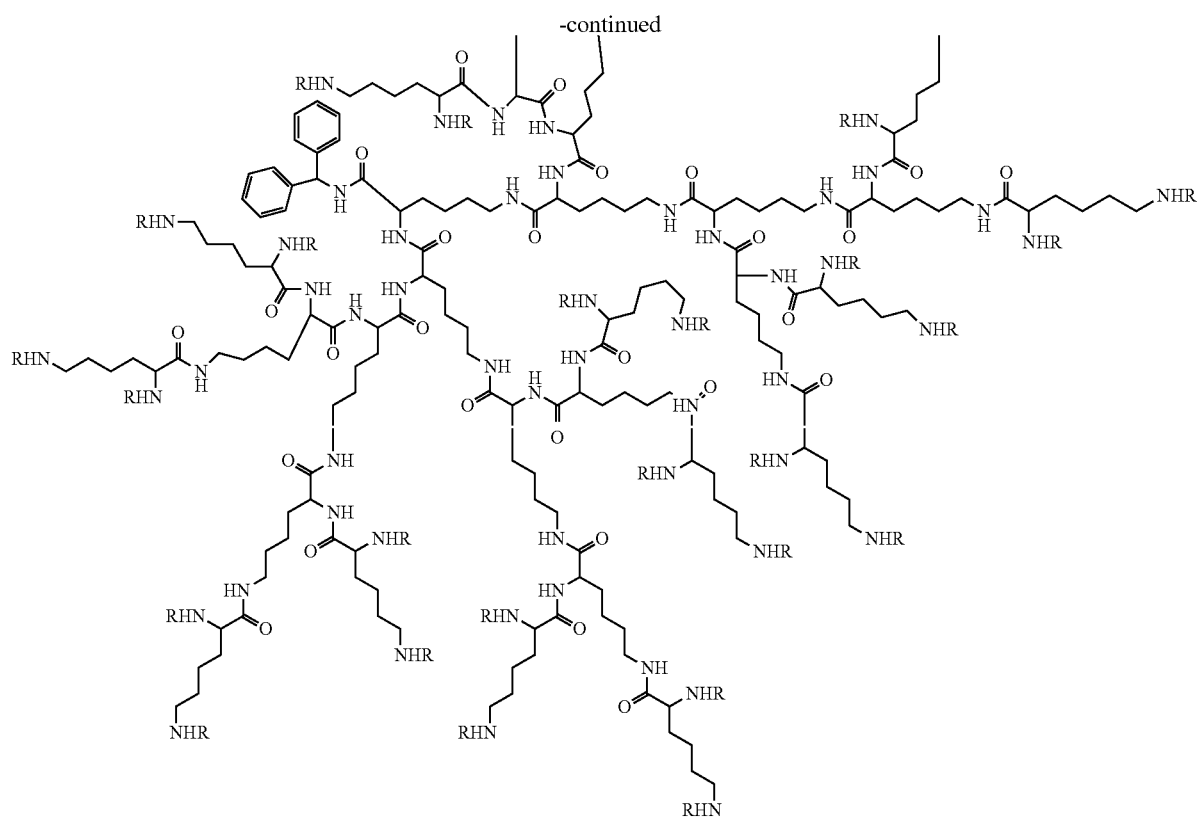
32. The composition according to claim 14, wherein the sulfonic acid-containing moiety is selected from the group consisting of:
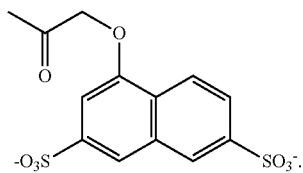
wherein R is
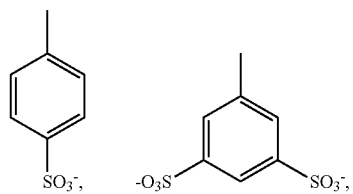
-continued
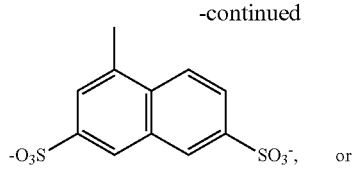
33. The composition according to claim 14, wherein the dendrimer comprises lysine building units.
34. The composition according to claim 14, wherein the dendrimer is

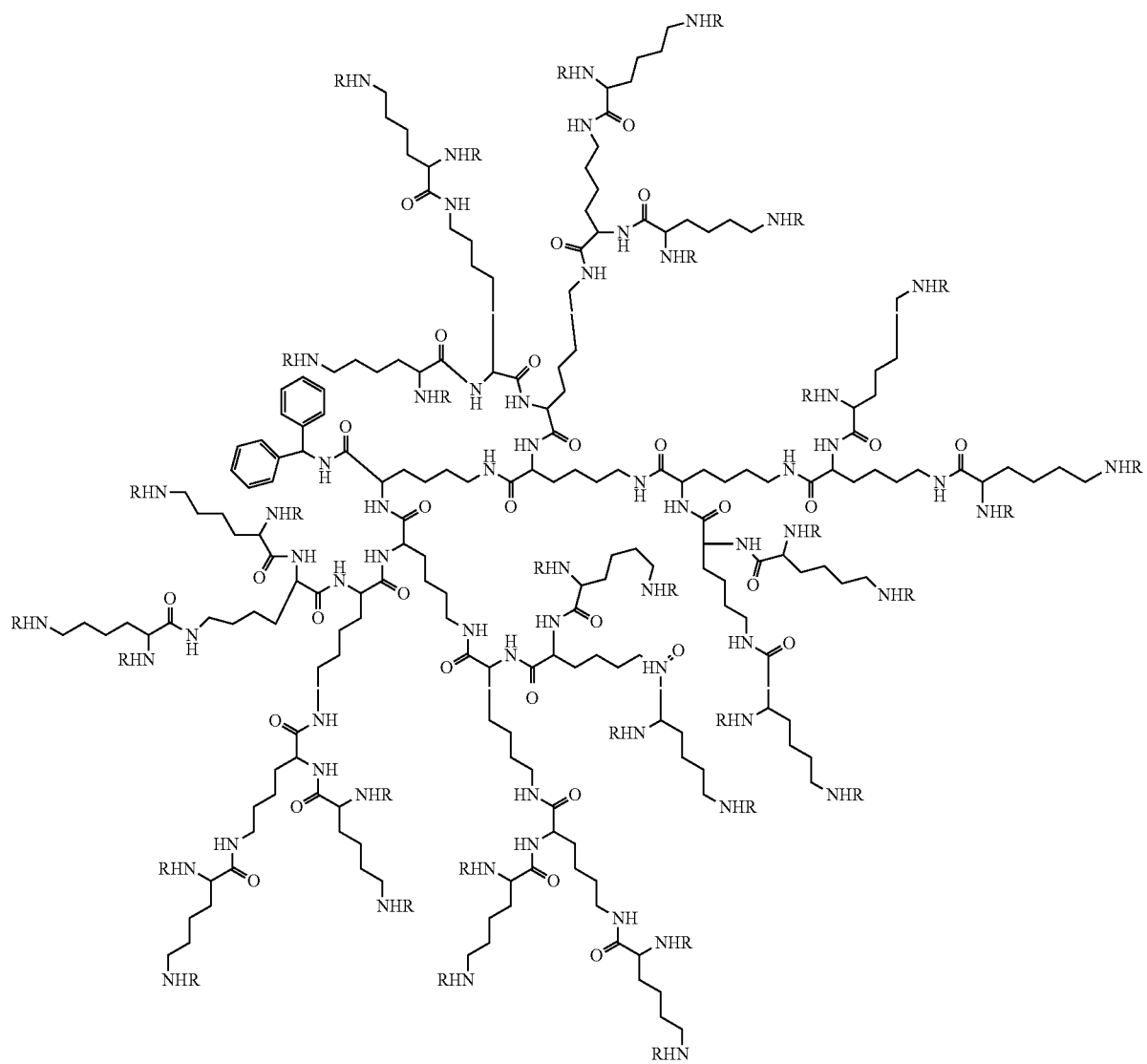
35. The solution according to claim 16, wherein the sulfonic acid-containing moiety is selected from the group consisting of:
wherein R is
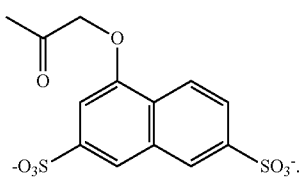
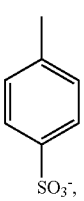
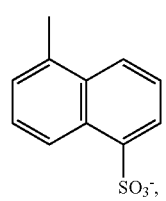
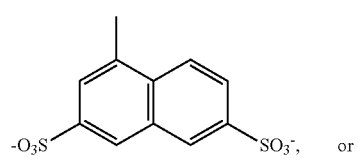
or

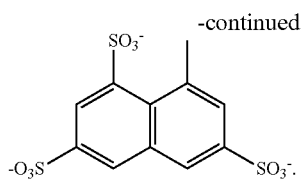

36. The solution according to claim 16, wherein the dendrimer comprises lysine building units.

37. The solution according to claim 36, wherein the dendrimer is

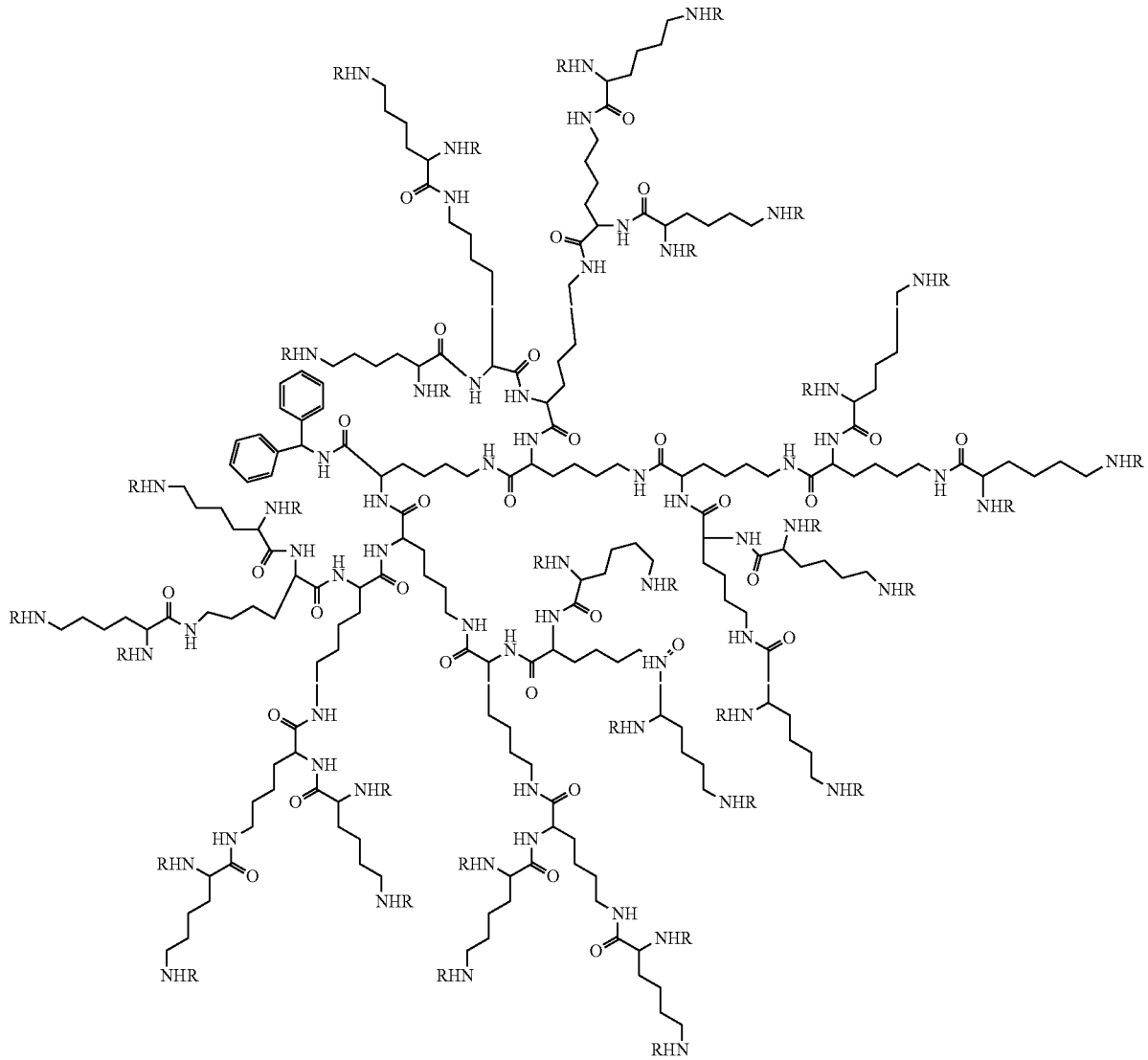

wherein R is

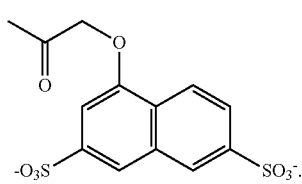

38. The method according to claim 1, wherein the macromolecule or pharmaceutically acceptable salt thereof is administered with an antiviral agent, an antibiotic, an anti-inflammatory or a corticosteroid.

39. The method according to claim 38, wherein the antibiotic is selected from the group consisting of amikacin, azithromycin, ceflixime, cefoperazone, cefotaxime, ceftazadime, ceftizoxime, ceftrioxone, chloramphenicol, ciprofloxacin, clindamycin, colistin, domeclocycline, erythromycin, gentamicin, mafenide, methacycline, neomycin, norfloxacin, ofloxacin, oxytetracycline, polymyxin B, pyrimethamine, rifaximin, silver sulfadiazine, sulfacetamide, sulfasoxazole, tetracycline and tobramycin.

40. The composition according to claim 14, wherein the macromolecule or pharmaceutically acceptable salt thereof is administered with an antiviral agent, an antibiotic, an anti-inflammatory or a corticosteroid.

41. The composition according to claim 40, wherein the antibiotic is selected from the group consisting of amikacin, azithromycin, ceflixime, cefoperazone, cefotaxime, ceftazadime, ceftizoxime, ceftrioxone, chloramphenicol, ciprofloxacin, clindamycin, colistin, domeclocycline, erythromycin, gentamicin, mafenide, methacycline, neomycin, norfloxacin, ofloxacin, oxytetracycline, polymyxin B, pyrimethamine, rifaximin, silver sulfadiazine, sulfacetamide, sulfasoxazole, tetracycline and tobramycin.

42. The method according to claim 3 wherein the adenovirus is adenovirus subtype 19 or 37.

43. The composition according to claim 19 wherein the adenovirus is adenovirus subtype 19 or 37.

* * * * *

UNITED STATES PATENT AND TRADEMARK OFFICE
CERTIFICATE OF CORRECTION

PATENT NO. : 10,149,885 B2
APPLICATION NO. : 14/427970
DATED : December 11, 2018
INVENTOR(S) : Jacinth Kincaid Fairley et al.

It is certified that error appears in the above-identified patent and that said Letters Patent is hereby corrected as shown below:

In the Specification

In Column 1, Line 34, change "Conjuctival" to --Conjunctival--.

In Column 2, Line 49, change "eyedrops" to --eye drops--.

In Column 5, Lines 18-19, change "conjuctiva" to --conjunctiva--.

In Column 5, Line 32, change "rikettsial" to --rickettsial--.

In Column 5, Line 32, change "(phlycentular" to --(phlyctenular--.

In Column 5, Line 35, change "pharyngoconjuctival" to --pharyngoconjunctival--.

In Column 6, Line 5, change "pyrogenes," to --pyogenes,--.

In Column 6, Line 6, change "Staphylcoccus" to --Staphylococcus--.

In Column 6, Line 7, change "aegyptus" to --aegyptius--.

In Column 6, Line 9, change "Psecudomonas" to --Pseudomonas--.

In Column 6, Lines 10-11, change "monocvtogenes," to --monocytogenes,--.

In Column 6, Line 11, change "iwoffi," to --lwoffii,--.

In Column 6, Line 14, change "foruitum," to --fortuitum,--.

In Column 6, Line 16, change "lymphogranulomatis" to --lymphogranulomatosis--.

Signed and Sealed this
Twenty-seventh Day of August, 2019

Andrei Iancu
*Director of the United States Patent and Trademark Office*

In Column 6, Line 17, change "spp." to --spp.,--.

In Column 6, Line 18, change "Haemophihts" to --Haemophilus--.

In Column 8, Line 13, change "H7N7." to --H7N7,--.

In Column 8, Line 18, change "pyrogenes," to --pyogenes,--.

In Column 8, Line 21, change "aegyptus" to --aegyptius--.

In Column 8, Line 22, change "Psecudomonas" to --Pseudomonas--.

In Column 8, Line 24, change "iwoffi," to --lwoffii,--.

In Column 8, Line 27, change "foruitum," to --fortuitum,--.

In Column 8, Line 29, change "lymphogranulomatis" to --lymphogranulomatosis--.

In Column 10, Line 35, change "ceflixime," to --cefixime,--.

In Column 10, Line 35, change "ceftazadime," to --ceftazidime,--.

In Column 10, Line 36, change "ceftrioxone," to --ceftriaxone,--.

In Column 10, Line 37, change "domeclocycline," to --demeclocycline,--.

In Column 10, Line 40, change "sulfasoxazole," to --sulfisoxazole,--.

In Column 10, Line 43, change "diflunisil" to --diflunisal--.

In Column 10, Line 45, change "ketaprofen," to --ketoprofen,--.

In Column 10, Line 45, change "flubiprofen," to --flurbiprofen,--.

In Column 10, Line 46, change "laxoprofen;" to --loxoprofen;--.

In Column 10, Line 47, change "keorolac," to --ketorolac,--.

In Column 10, Lines 48-49, change "maloxicam," to --meloxicam,--.

In Column 10, Line 50, change "mefanamic" to --mefenamic--.

In Column 10, Line 56, change "prednisilone," to --prednisolone,--.

In Column 10, Line 57, change "prednisilone," to --prednisolone,--.

In Column 10, Line 57, change "triamcinolore" to --triamcinolone--.

In Column 10, Lines 57-58, change "trimcinolone" to --triamcinolone--.

In Column 10, Line 58, change "mometasome," to --mometasone,--.

In Column 10, Line 59, change "fluocinide," to --fluocinonide,--.

In Column 10, Line 61, change "cloberasome-" to --clobetasone- --.

In Column 12, Line 51 (Approx.), change "mercaptoakylamines," to --mercaptoalkylamines,--.

In Column 14, Line 29 (Approx.), change "N:" to --N;--.

In Columns 17-18, Line 67 (Approx.), change " 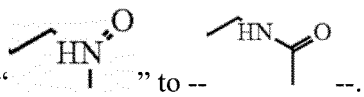 " to -- 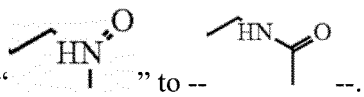 --.

In Columns 21-22, Lines 1-65 (Approx.), change " 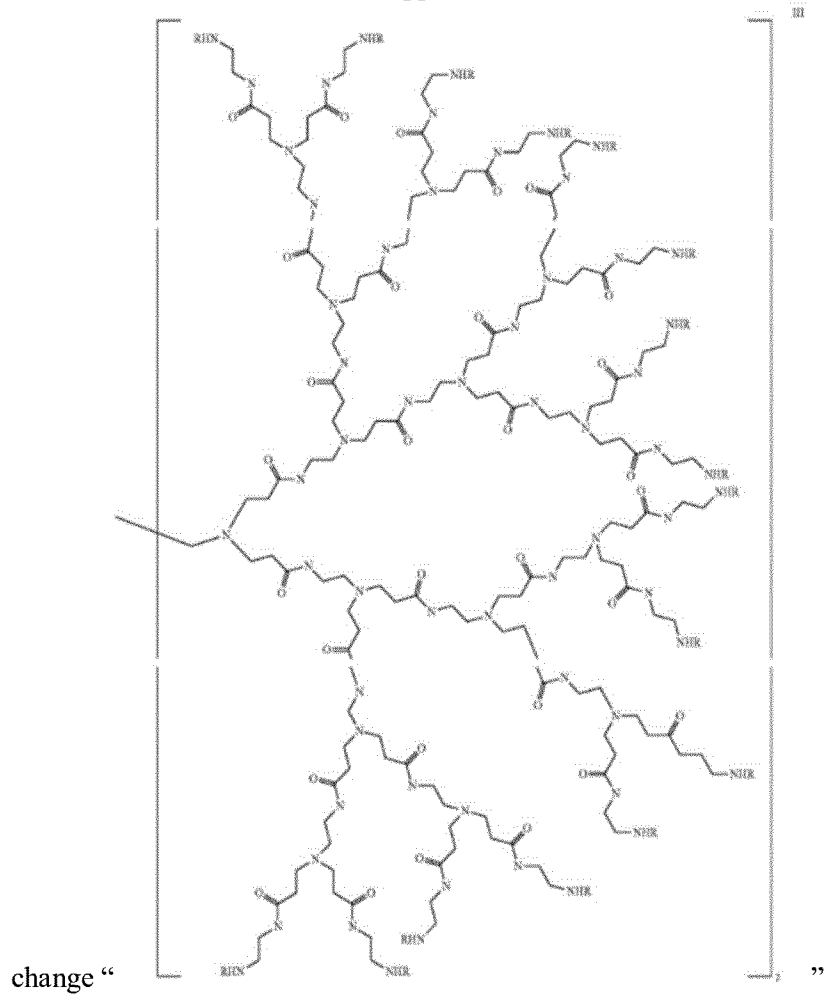 "

to -- 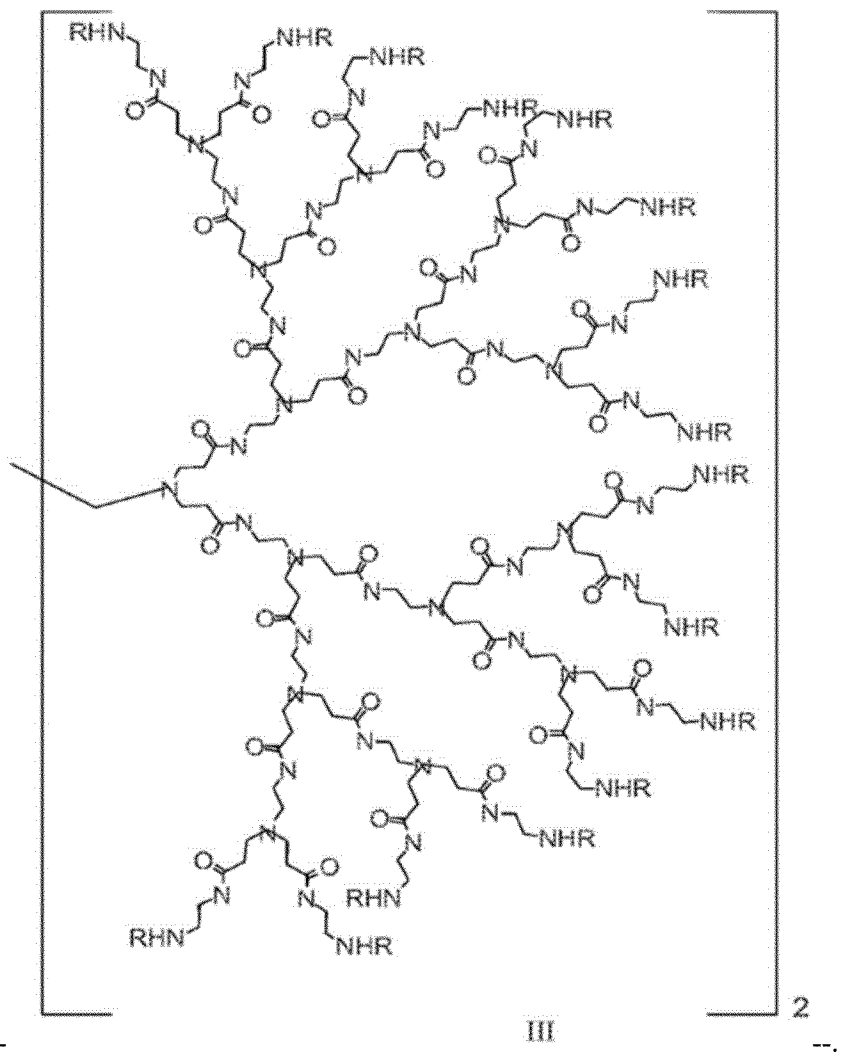 --.

In Column 24, Line 26, change "mucuric" to --mercuric--.

In Column 24, Line 50, change "carageenan," to --carrageenan,--.

In Column 25, Line 26, change "aerugenosa" to --aeruginosa--.

In Column 26, Line 35, change "hours" to --hours.--.

In Column 26, Line 43 (Approx.), change "biquanide" to --biguanide--.

In Column 27, Line 49, change "37(4)." to --37(4),--.

In Column 28, Line 13, change "Bioaasay." to --Bioassay.--.

In Column 28, Line 34 (Approx.), change "adenoviridiae" to --adenoviridae--.

CERTIFICATE OF CORRECTION (continued)
U.S. Pat. No. 10,149,885 B2

In Column 29, Line 5, change "IC$_{50}$Cidovofir" to --IC$_{50}$Cidofovir--.

In Column 29, Line 25 (Approx.), change "see," to --sec,--.

In Column 29, Line 37 (Approx.), change "TCID$_5$," to --TCID$_{50}$--.

In Column 30, Line 66, change "Ribivirin" to --Ribavirin--.

In Columns 31-32, Line 40 (Approx.), change "Neutralizalion" to --Neutralization--.

In Column 33, Line 23, change "<51>"Antimicrobial" to --<51> "Antimicrobial--.

In Column 33, Line 34 (Approx.), change "Staphycocccus" to --Staphylococcus--.

In Column 33, Line 62, change "bacteriocide" to --bactericide--.

In Column 38, Line 53, change "%-well" to --96-well--.

In Column 39, Line 30 (Approx.), change "4153)." to --4153),--.

In Column 39, Line 54 (Approx.), after "passage" insert --5--.

In Column 40, Line 39 (Approx.), change "82:377-390.)." to --82:377-390.)--.

In the Claims

In Column 41, Line 41, Claim 4, after "according" insert --to--.

In Column 41, Lines 43-44, Claim 4, change "keratoconjuctivitis," to --keratoconjunctivitis,--.

In Column 43, Lines 40-41 (Approx.), Claim 20, change "keratoconjuctivitis," to --keratoconjunctivitis,--.

In Columns 45-46, Line 16 (Approx.), Claim 31, change " 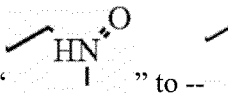 " to -- 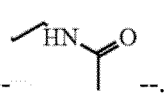 --.

In Columns 47-48, Line 26 (Approx.), Claim 34, change " 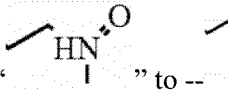 " to -- 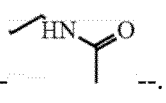 --.

In Columns 49-50, Line 42 (Approx.), Claim 37, change " 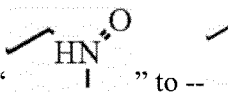 " to -- 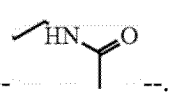 --.

In Column 50, Line 7, Claim 39, change "ceflixime," to --cefixime,--.

CERTIFICATE OF CORRECTION (continued)
U.S. Pat. No. 10,149,885 B2

In Column 50, Lines 7-8, Claim 39, change "ceftazadime," to --ceftazidime,--.

In Column 50, Line 8, Claim 39, change "ceftrioxone," to --ceftriaxone,--.

In Column 50, Line 9, Claim 39, change "domeclocycline," to --demeclocycline,--.

In Column 50, Line 58, Claim 39, change "sulfasoxazole," to --sulfisoxazole,--.

In Column 50, Line 65, Claim 41, change "ceflixime," to --cefixime,--.

In Column 50, Lines 65-66, Claim 41, change "ceftazadime," to --ceftazidime,--.

In Column 50, Line 66, Claim 41, change "ceftrioxone," to --ceftriaxone,--.

In Column 50, Line 67, Claim 41, change "domeclocycline," to --demeclocycline,--.

In Column 51, Line 4, Claim 41, change "sulfasoxazole," to --sulfisoxazole,--.